(12) United States Patent
Bryson et al.

(10) Patent No.: US 11,896,811 B2
(45) Date of Patent: Feb. 13, 2024

(54) IMPLANTABLE VENTRICULAR ASSIST DEVICES AND METHODS

(71) Applicant: W. L. Gore & Associates, Inc., Newark, DE (US)

(72) Inventors: Scott M. Bryson, Flagstaff, AZ (US); Dustin C. Burkart, Bellemont, AZ (US); Zachary A. Crannell, Flagstaff, AZ (US); Joshua D. Cross, Flagstaff, AZ (US); Robert M. Depue, Flagstaff, AZ (US); James L. Goepfrich, Flagstaff, AZ (US); Paul D. Goodman, Flagstaff, AZ (US); Brandon C. Hedberg, Flagstaff, AZ (US); Jason D. Hemmer, Flagstaff, AZ (US); Jeffrey Kennington, Flagstaff, AZ (US); Elton R. Migliati, Flagstaff, AZ (US); Bryan Reep, Flagstaff, AZ (US); Edward E. Shaw, Flagstaff, AZ (US); James D. Silverman, Flagstaff, AZ (US); Richard D. Strones, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 429 days.

(21) Appl. No.: 16/577,565

(22) Filed: Sep. 20, 2019

(65) Prior Publication Data
US 2020/0139032 A1   May 7, 2020

Related U.S. Application Data

(60) Provisional application No. 62/844,447, filed on May 7, 2019, provisional application No. 62/833,063, filed
(Continued)

(51) Int. Cl.
*A61M 60/148* (2021.01)
*A61M 60/178* (2021.01)
(Continued)

(52) U.S. Cl.
CPC ........ *A61M 60/148* (2021.01); *A61M 60/178* (2021.01); *A61M 60/232* (2021.01);
(Continued)

(58) Field of Classification Search
CPC .............. A61M 60/147; A61M 60/135; A61M 60/857; A61M 60/50; A61N 1/3962; A61B 5/0031
See application file for complete search history.

(56) References Cited

U.S. PATENT DOCUMENTS 4,776,337 A    10/1988  Palmaz
6,136,025 A *  10/2000  Barbut ................ A61M 60/867
                                                        623/3.15
(Continued)

FOREIGN PATENT DOCUMENTS

EP    2727612 A1    5/2014
JP    2002-536079 A 10/2002
(Continued)

OTHER PUBLICATIONS

International Search Report and Written Opinion received for PCT Patent Application No. PCT/US2019/028622, dated Jul. 25, 2019, 11 pages.
(Continued)

*Primary Examiner* — Lindsey G Wehrheim

(57) ABSTRACT

Various aspects of the present disclosure are directed toward implantable medical devices, systems, and methods for cardiac assistance.

42 Claims, 27 Drawing Sheets

Related U.S. Application Data on Apr. 12, 2019, provisional application No. 62/791,484, filed on Jan. 11, 2019, provisional application No. 62/791,477, filed on Jan. 11, 2019, provisional application No. 62/754,655, filed on Nov. 2, 2018.

(51) Int. Cl.

| | | |
|---|---|---|
| *A61N 1/39* | (2006.01) | |
| *A61M 60/857* | (2021.01) | |
| *A61M 60/408* | (2021.01) | |
| *A61M 60/232* | (2021.01) | |
| *A61M 60/508* | (2021.01) | |
| *A61B 5/00* | (2006.01) | |

(52) U.S. Cl.
CPC ........ *A61M 60/408* (2021.01); *A61M 60/508* (2021.01); *A61M 60/857* (2021.01); *A61N 1/3962* (2013.01); *A61B 5/0031* (2013.01)

(56) References Cited

U.S. PATENT DOCUMENTS

| | | | |
|---|---|---|---|
| 6,400,991 B1 | 6/2002 | Kung | |
| 6,645,242 B1 | 11/2003 | Quinn | |
| 7,039,450 B2* | 5/2006 | Duarte | A61B 5/287 |
| | | | 600/374 |
| 8,992,545 B2 | 3/2015 | Cahill | |
| 9,492,600 B2 | 11/2016 | Strueber et al. | |
| 9,554,806 B2 | 1/2017 | Larsen et al. | |
| 9,839,734 B1 | 12/2017 | Menon et al. | |
| 2003/0100816 A1 | 5/2003 | Siess | |
| 2005/0049696 A1 | 3/2005 | Siess et al. | |
| 2010/0249489 A1* | 9/2010 | Jarvik | A61M 60/205 |
| | | | 600/16 |
| 2012/0059459 A1 | 3/2012 | Asirvatham et al. | |
| 2015/0005810 A1 | 1/2015 | Center et al. | |
| 2015/0245840 A1 | 9/2015 | Farnan | |
| 2015/0250935 A1 | 9/2015 | Anderson et al. | |
| 2015/0258260 A1 | 9/2015 | Tuseth | |
| 2016/0331382 A1 | 11/2016 | Center et al. | |
| 2017/0209633 A1 | 7/2017 | Cohen | |
| 2017/0232170 A1 | 8/2017 | Jarvik | |
| 2017/0325930 A1 | 11/2017 | Montgomery et al. | |
| 2018/0193543 A1 | 7/2018 | Sun | |
| 2019/0110893 A1 | 4/2019 | Haarer et al. | |
| 2019/0125534 A1 | 5/2019 | Arcaro et al. | |
| 2019/0321528 A1 | 10/2019 | Coffman | |

FOREIGN PATENT DOCUMENTS

| | | |
|---|---|---|
| JP | 2003-528697 A | 9/2003 |
| JP | 2013-504370 A | 2/2013 |
| JP | 2014-091049 A | 5/2014 |
| JP | 2016-516551 A | 6/2016 |
| JP | 2017-502644 A | 1/2017 |
| JP | 2017-507727 A | 3/2017 |
| WO | 2011/031364 A1 | 3/2011 |
| WO | 2013/148697 A1 | 10/2013 |
| WO | 2014/179391 A2 | 11/2014 |
| WO | 2015/134661 A1 | 9/2015 |

OTHER PUBLICATIONS

International Search Report and Written Opinion received for PCT Patent Application No. PCT/US2019/052185, dated Mar. 24, 2020, 21 pages.

* cited by examiner

IMPLANTABLE VENTRICULAR ASSIST DEVICES AND METHODS

CROSS-REFERENCE TO RELATED APPLICATION

This application claims the benefit of Provisional Application No. 62/754,655, filed Nov. 2, 2018, Provisional Application No. 62/791,484, filed Jan. 11, 2019, Provisional Application No. 62/791,477, filed Jan. 11, 2019, Provisional Application No. 62/833,063, filed Apr. 12, 2019, and Provisional Application No. 62/844,447, filed May 7, 2019, all of which are incorporated herein by reference in their entireties for all purposes.

FIELD

The present disclosure relates generally to medical devices and more specifically to implantable ventricular assist devices and supporting structures configured to operate within a patient's vasculature and that can be minimally invasively delivered via a catheter.

BACKGROUND

Cardiac assist devices (CAD) generally relate to systems that include a pump that assists heart function without replacing the heart in order to improve hemodynamics. Depending on the needs and demands of the patient, the pump may be placed outside the patient's body (extra- or para-corporeal devices), or within the patient's abdomen such as in the pericardial cavity beneath or above the diaphragm (intracorporeal device). Attempts have also been made to place such pumps within the patient's vasculature, including within the heart itself.

SUMMARY

According to one example ("Example 1"), an implantable medical device for cardiac assistance includes a main body configured to deploy within the aorta and including a lumen maintaining fluid flow through the aorta and an access site in a sidewall of the main body providing access to the lumen of the main body; and a branch member configured to deploy within the access site to fluidly connect with the lumen of the main body and including a pump configured to force blood flow through the branch member and into the lumen of the main body.

According to another example ("Example 2"), further to the implantable medical device of Example 1, the branch member is configured to implant within an atrium or a ventricle of a patient.

According to another example ("Example 3"), further to the implantable medical device of Example 2, the pump is configured to increase blood flow into the aorta for cardiac assistance.

According to another example ("Example 4"), the implantable medical device of any one of Examples 1-2, the branch member includes a sealing element near a first end configured to engage a tissue wall of the atrium or the left ventricle.

According to another example ("Example 5"), further to the implantable medical device of Example 4, the sealing element comprises a polymeric material.

According to another example ("Example 6"), further to the implantable medical device of Example 4, the flange configured to engage the tissue wall in a fluid tight fluid communication between the branch member and the lumen of the main body.

According to another example ("Example 7"), the implantable medical device of any one of Examples 1-6, the access site in the main body includes a fenestration and the branch member is configured to seal within the fenestration to fluidly connect the branch and the main body.

According to another example ("Example 8"), the implantable medical device of any one of Examples 1-6, the device further includes a portal arranged within the main lumen aligned with the access site in the main body, and the branch member is configured to implant within the portal to fluidly connect the branch and the main body.

According to another example ("Example 9"), the implantable medical device of any one of Examples 1-8, the pump is removably coupled to the branch member.

According to another example ("Example 10"), further to the implantable medical device of Example 9, the pump is configured to anchor within the branch member.

According to another example ("Example 11"), the implantable medical device of any one of Examples 1-10, the branch is configured to implant within the aorta adjacent or between an aortic valve.

According to another example ("Example 12"), the implantable medical device of any one of Examples 1-11, the pump is powered remotely.

According to another example ("Example 13"), the implantable medical device of any one of Examples 1-12, the branch member is configured to couple the atrium and the aorta and allow independent motion of the atrium and the aorta.

According to another example ("Example 14"), the implantable medical device of any one of Examples 1-13, the pump is configured to deliver the blood flow through the branch member and into the lumen of the main body parallel to natural blood flow through the aorta.

According to one example ("Example 15"), a system for implanting an implantable medical device for cardiac assistance including a first catheter configured to deploy an implantable medical device within an aorta, the implantable medical device including a main body and a lumen maintaining fluid flow through the aorta and an access site in a sidewall of the main body providing access to the lumen of the main body; and a second catheter configured to deploy a branch member within the access site to fluidly connect with the lumen of the main body and including a pump configured to force blood flow through the branch member and into the lumen of the main body.

According to another example ("Example 16"), further to the system of Example 15, the second catheter is configured to deploy the branch member transapically.

According to another example ("Example 17"), further to the system of Example 15, the second catheter is configured to deploy the branch member transseptally.

According to another example ("Example 18"), the system of any one of Examples 15-17, the system also includes a puncture device configured to create an access site in the aorta and an access site in an atrium or ventricle, and wherein the second catheter is configured to deploy the branch member across the access site in the aorta and the access site in an atrium or left ventricle.

According to another example ("Example 19"), further to the system of Example, the second catheter includes a sheath configured to deploy a flange arranged with a distal end of the branch member, the flange configured to engage a tissue wall of the atrium or the ventricle in a fluid tight fluid communication between the branch member and the lumen of the main body.

According to one example ("Example 20"), method for implanting an implantable medical device for cardiac assistance includes arranging a first catheter within the aorta to deploy an implantable medical device within the aorta, the implantable medical device including a main body and a lumen maintaining fluid flow through the aorta and an access site in a sidewall of the main body providing access to the lumen of the main body; and arranging a second catheter within the access site to fluidly connect a branch member with the lumen of the main body, the branch member including a pump configured to force blood flow through the branch member and into the lumen of the main body.

According to another example ("Example 21"), further to the method of Example 21, the second catheter is configured to deploy the branch member transapically.

According to another example ("Example 22"), further to the method of Example 22, the second catheter is configured to deploy the branch member transseptally.

According to one example ("Example 23"), an implantable medical device for cardiac assistance includes a main body configured to deploy within an aorta, the main body including a lumen maintaining fluid flow through the aorta and an access site in a sidewall of the main body providing access to the lumen of the main body; a branch member configured to deploy within the access site to fluidly connect with the lumen of the main body and within a left atrial appendage of a heart; and a pump configured to force blood flow through the branch member and into the lumen of the main body.

According to another example ("Example 24"), further to the device of Example 23, the device also includes a stent structure coupled to the branch member or the pump and configured to stabilize the branch member or the pump within the left atrial appendage.

According to another example ("Example 25"), further to the device of Example 24, the branch member or the pump is arranged through an eyelet of the stent structure.

According to another example ("Example 26"), further to the device of Example 25, the stent structure includes an acorn shape or a shape that tapers toward a distal end.

According to one example ("Example 27"), an implantable medical device for cardiac assistance includes a branch member including a first end portion configured to deploy within a left atrial appendage of a heart and a second end portion configured to deploy within an aorta, the branch member being configured to interface with a pump to pass blood flow through a lumen of the branch member from the left atrial appendage into the aorta.

According to another example ("Example 28"), further to the device of Example 27, the devices also includes the pump configured to intake blood from the left atrial appendage and discharge the blood into the aorta.

According to another example ("Example 29"), further to the device of Example 28, the outflow of the pump is directly implanted into the aorta through the branch member.

According to another example ("Example 30"), further to the device of Example 29, the second end portion includes a flange configured to engage the tissue wall in a fluid tight fluid communication between the branch member and the tissue wall of the aorta.

According to another example ("Example 31"), further to the device of Example 30, the device also includes a stent structure coupled to the branch member and configured to stabilize the branch member or the pump within the left atrial appendage.

According to one example ("Example 32"), an implantable medical device for cardiac assistance includes a main body configured to deploy within the aorta and including a lumen maintaining fluid flow through the aorta and an access site in a sidewall of the main body providing access to the lumen of the main body; a branch member configured to deploy within the access site to fluidly connect with the lumen of the main body; and a pump arranged within a chamber of the heart and configured to force blood flow through the branch member and into the lumen of the main body.

According to another example ("Example 33"), further to the implantable medical device of Example 32, the branch member is arranged about a patient's heart.

According to another example ("Example 34"), further to the implantable medical device of Example 33, the pump is configured to implant within a left ventricle of the patient's heart and force blood flow through the branch member and into the lumen of the main body.

According to another example ("Example 35"), further to the implantable medical device of any one of Examples 32-34, the main body and the branch member form a non-surgical anastomosis with the aorta and the pump is configured to direct the blood flow into the aorta in line with or parallel to native flow.

According to one example ("Example 36"), an implantable medical device for cardiac assistance includes a pump configured to deploy within a pulmonary vein and including a lumen maintaining fluid flow through the pulmonary vein and configured to force blood flow through the lumen.

According to another example ("Example 37"), further to the implantable medical device of Example 35, the pump is configured to intake blood from the pulmonary vein and discharge the blood into the left atrium.

According to another example ("Example 38"), further to the implantable medical device of any one of Examples 35-36, the pump is configured to increase flow out of the pulmonary vein to increase cardiac output.

According to another example ("Example 39"), further to the implantable medical device of any one of Examples 35-38, the device also includes a driveline configured to power the pump and arranged out of the pulmonary vein into the left atrium and across a septum to exit a right side of the heart.

According to another example ("Example 40"), further to the implantable medical device of Example 39, the driveline exits a patient via an iliac vein.

According to one example ("Example 41"), a method for cardiac assistance includes arranging an implantable medical device between an aorta and a heart chamber of a patient, the implantable medical device including a pump configured to force blood flow from the heart chamber into the aorta; and forming a conduit of native tissue about the pump and between the aorta and the heart chamber.

According to another example ("Example 42"), further to the method of Example 41, forming the conduit of native tissue includes creating scarring or tissue ingrowth to form a tissue layer between the aorta and the heart chamber.

According to another example ("Example 43"), further to the method of any one of Examples 41-42, the pump includes a material arranged about an outer surface of the pump configured to facilitate tissue ingrowth.

According to another example ("Example 44"), further to the method of Example 42, the material includes at least one of Dacron and ePTFE.

According to an example ("Example 45"), a medical device for cardiac assistance includes a prosthetic valve comprising: a support frame, a plurality of leaflets coupled to the support frame and configured to open to allow forward flow therethrough and to occlude the support frame to prevent retrograde flow, and a pump arranged with the support frame and configured to force blood through the support frame.

According to another example ("Example 46"), further to the medical device of Example 45, the plurality of leaflets are configured to coapt about the pump arranged within the support frame.

According to another example ("Example 47"), further to the medical device of Example 46, the pump is arranged centrally within the support frame.

According to another example ("Example 48"), further to the medical device of any one of Examples 45-47, the device also includes a filter arranged at an outflow end of the support frame.

According to another example ("Example 49"), further to the medical device of Example 48, wherein the filter is arranged on an outflow end of the pump.

According to another example ("Example 50"), further to the medical device of any one of Examples 45-49, the prosthetic valve is configured to replace an aortic valve of a patient.

According to another example ("Example 51"), further to the medical device of any one of Examples 45-50, the prosthetic valve is configured to replace a mitral valve of a patient.

According to another example ("Example 52"), further to the medical device of any one of Examples 45-51, the prosthetic valve and the pump are configured to transcatheter delivery.

According to one example ("Example 53"), an implantable medical device for cardiac assistance includes a main body configured to deploy within the aorta and including a lumen maintaining fluid flow through the aorta; a branch member extending from the main body and configured to deploy within a chamber of the heart to fluidly connect the aorta and the chamber of the heart; and a pump arranged within the branch member and configured to force blood flow from the chamber of the heart through the branch member and into the lumen of the main body.

According to another example ("Example 54"), further to the medical device of Example 53, the branch member is integral with the main body.

According to another example ("Example 55"), further to the medical device of Example 53, the branch member is configured to telescope inwardly and outwardly relative to the main body.

According to one example ("Example 56"), a method of deploying the medical device of any one of Examples 53-55 includes deploying the main body within the aorta; creating openings in the aorta and in the chamber of the heart; and deploying the branch member across the aorta and the chamber of the heart.

According to one example ("Example 57"), an implantable medical device for cardiac assistance includes a main body configured to deploy within the aorta and including a lumen maintaining fluid flow through the aorta and an access site in a sidewall of the main body providing access to the lumen of the main body; and a branch member configured to deploy within the access site to fluidly connect with the lumen of the main body and interface with a pump to pass blood flow through the branch member into the main body.

According to another example ("Example 58"), further to the medical device of Example 57, the branch member is configured to anchor the pump within the branch member.

According to another example ("Example 59"), further to the medical device of Example 58, the branch member includes an attachment mechanism configured to anchor the pump within the branch member.

According to another example ("Example 60"), further to the medical device of any one of Examples 58-59, the branch member and the pump include complementary attachment mechanisms to anchor the pump within the branch member.

According to another example ("Example 61"), further to the medical device of any one of Examples 58-60, the branch member is configured to frictionally engage with the pump to anchor the pump within the branch member.

According to another example ("Example 62"), a method of deploying the medical device of any one of Examples 58-61 includes deploying the main body within the aorta; creating openings in the aorta and in the chamber of the heart; and deploying the branch member across the aorta and the chamber of the heart.

According to one example ("Example 63") a medical device for cardiac assistance includes a prosthetic valve having a support frame configured to implant within the patient and interface with a pump to pass blood flow therethrough; and a plurality of leaflets coupled to the support frame and configured to open to allow forward flow therethrough and to occlude the support frame to prevent retrograde flow.

According to another example ("Example 64"), further to the medical device of Example 63, the support frame is configured to anchor the pump within the branch member.

According to another example ("Example 65"), further to the medical device of Example 64, the support frame includes an attachment mechanism configured to anchor the pump within the branch member.

According to another example ("Example 66"), further to the medical device of any one of Examples 64-65, the support frame and the pump include complementary attachment mechanisms to anchor the pump within the branch member.

According to another example ("Example 67"), further to the medical device of any one of Examples 63-64, wherein the support frame is configured to frictionally engage with the pump to anchor the pump within the branch member.

According to one example ("Example 68"), an implantable medical device for cardiac assistance includes a main body configured to deploy within the aorta and including a lumen maintaining fluid flow through the aorta; and a branch member extending from the main body and configured to deploy within a chamber of the heart to fluidly connect the aorta and the chamber of the heart and interface with a pump to pass blood flow through the branch member into the main body.

According to another example ("Example 69"), further to the medical device of Example 68, the branch member is configured to anchor the pump within the branch member.

According to another example ("Example 70"), further to the medical device of Example 69, the branch member includes an attachment mechanism configured to anchor the pump within the branch member.

According to another example ("Example 71"), further to the medical device of any one of Examples 69-70, the branch member and the pump include complementary attachment mechanisms to anchor the pump within the branch member.

According to another example ("Example 72"), further to the medical device of any one of Examples 66-71, the branch member is configured to frictionally engage with the pump to anchor the pump within the branch member.

According to one example ("Example 73"), an implantable medical device for cardiac assistance includes a stent-graft configured to deploy within a pulmonary vein and including a lumen maintaining fluid flow through the pulmonary vein and configured to interface with a pump to pass blood flow through the lumen.

According to another example ("Example 74"), further to the medical device of Example 73, further including the pump configured to intake blood from the pulmonary vein and discharge the blood into the left atrium.

According to one example ("Example 75") an implantable medical device for cardiac assistance includes a main body configured to deploy within the aorta and including a lumen maintaining fluid flow through the aorta and an access site in a sidewall of the main body providing access to the lumen of the main body; a branch member configured to deploy within the access site to fluidly connect with the lumen of the main body; and a pump configured to force blood flow through the branch member and into the lumen of the main body and including an anchor element configured to removably fix the pump within the branch member.

According to another example ("Example 76"), further to the implantable medical device of Example 75, the anchor element is at least one hinge structure configured to articulate a portion of the pump and maintain the pump in an angled configuration.

According to another example ("Example 77"), further to the implantable medical device of Example 76, the pump includes a tubular portion and the hinge structure is arranged circumferentially within or about the tubular portion.

According to another example ("Example 78"), further to the implantable medical device of Example 77, the hinge structure includes a plurality of discrete rings configured to maintain the tubular portion in the angled configuration in response to an applied force.

According to another example ("Example 79"), further to the implantable medical device of Example 75, the anchor element is arranged on an external surface of the pump and configured to expand and engage an interior surface of the branch member.

According to another example ("Example 80"), further to the implantable medical device of Example 79, the anchor element is an expandable balloon configured to expand and engage an interior surface of the branch member.

According to another example ("Example 81"), further to the implantable medical device of Example 80, the expandable balloon is arranged circumferentially about the pump.

According to another example ("Example 82"), further to the implantable medical device of Example 79, the anchor element is spring arranged on the external surface of the pump and an expandable balloon is configured to collapse the spring in response to inflation.

According to another example ("Example 83"), further to the implantable medical device of Example 75, wherein the anchor element includes a plurality of flanges extending radially from an end portion of the pump.

According to another example ("Example 84"), further to the implantable medical device of Example 75, the device also includes a receiving structure arranged on an internal surface of the branch member and wherein the anchor element is configured to engage the receiving structure to removably fix the pump within the branch member.

According to another example ("Example 85"), further to the implantable medical device of Example 84, the anchor element is a stent and the receiving structure is configured to contain the stent to removably fix the pump within the branch member.

According to another example ("Example 86"), further to the implantable medical device of Example 84, the anchor element is a protrusion and the receiving structure is a shaped notch configured to contain the protrusion to removably fix the pump within the branch member.

According to another example ("Example 87"), further to the implantable medical device of Example 84, the anchor element is a first threaded member and the receiving structure is a second threaded member and the first threaded member and the second threaded member are configured to engage to removably fix the pump within the branch member.

According to another example ("Example 88"), further to the implantable medical device of any one of Examples 86-87, the pump is configured to facilitate engagement between the anchor element and the receiving structure.

According to an example ("Example 89"), an implantable medical device for cardiac assistance includes a main body configured to deploy within the aorta and including a lumen maintaining fluid flow through the aorta and an access site in a sidewall of the main body providing access to the lumen of the main body; and a pump configured to deploy within the access site and to force blood flow through the pump and into the lumen of the main body, the pump including an expandable braided structure configured to removably fix the pump within the main body.

According to another example ("Example 90"), further to the implantable medical device of Example 89, the expandable braided structure includes a snaring element configured to facilitate collapsing of the expandable braided structure in response to tension.

According to another example ("Example 91"), a method of deploying an implantable medical device for cardiac assistance includes arranging a main body within the aorta, the main body including a lumen maintaining fluid flow through the aorta and an access site in a sidewall of the main body providing access to the lumen of the main body; deploying a branch member within the access site to fluidly connect with the lumen of the main body; and anchoring a pump configured to force blood flow through the branch member and into the lumen of the main body with the branch member using an anchor element configured to removably fix the pump within the branch member.

According to another example ("Example 92"), further to the method of Example 91, the anchor element is at least one hinge structure configured to articulate a portion of the pump and maintain the pump in an angled configuration and anchoring the pump includes arranging the at least one hinge structure within the branch member.

According to another example ("Example 93"), further to the method of Example 91, the anchor element is arranged on an external surface of the pump and configured to expand and engage an interior surface of the branch member and anchoring the pump includes expanding and engaging the anchor element to engage the interior surface of the branch member.

According to another example ("Example 94"), further to the method of Example 91, the implantable medical device includes a receiving structure arranged on an internal surface of the branch member and anchoring the pump includes engaging the anchor element with the receiving structure to removably fix the pump within the branch member.

According to one example ("Example 95"), an implantable medical device for cardiac assistance includes a main body configured to be disposed within the aorta, the main body including a lumen operable to convey blood through the aorta; an access site in a sidewall of the main body operable to provide access to the lumen of the main body; and a branch member configured to be disposed within the access site to fluidly connect with the lumen of the main body, the branch member includes one or more anchor elements configured to interface with and secure a pump with the branch member.

According to another example ("Example 96"), further to the device of Example 95, the branch member is configured to be disposed within an atrium or a ventricle of a patient.

According to another example ("Example 97"), further to the device of Example 96, the device also includes the pump and the pump is configured to convey blood into the aorta from the atrium or ventricle for cardiac assistance through the branch member and into the main body.

According to another example ("Example 98"), further to the device of any one of Examples 95-97, the branch member includes a sealing element near a first end configured to engage a tissue wall of a left atrium or a left ventricle.

According to another example ("Example 99"), further to the device of Example 98, the sealing element includes a flange configured to engage the tissue wall.

According to another example ("Example 100"), further to the device of any one of Examples 95-99, the access site in the main body includes a fenestration, the branch member is configured to seal with the fenestration to fluidly connect the branch member and the main bod.

According to another example ("Example 101"), further to the device of any one of Examples 95-99, the device also includes a portal arranged within the main lumen that is aligned with the access site in the main body, and a first portion of the branch member is configured to be disposed within the portal to fluidly connect the branch member and the main body.

According to another example ("Example 102"), further to the device of any one of Examples 95-101, a second portion of the branch member is configured to be disposed within the access site to fluidly connect with the lumen of the main body and a left atrial appendage of a heart.

According to another example ("Example 103"), further to the device of Example 102, the device also includes a stent structure coupled to the branch member or the pump and configured to stabilize the branch member or the pump within the left atrial appendage.

According to another example ("Example 104"), further to the device of Example 103, the branch member or the pump is arranged through an eyelet of the stent structure.

According to another example ("Example 105"), further to the device of Example 104, the stent structure defines an acorn shape or a shape that tapers toward a distal end.

According to another example ("Example 106"), further to the device of Example 95, the branch member is arranged about a patient's heart.

According to another example ("Example 107"), further to the device of Example 95, the pump includes one or more pump anchor elements, wherein the one or more branch anchor elements are operable for cooperative engagement with the one or more pump anchor elements and configured to anchor the pump with the branch member.

According to another example ("Example 108"), further to the device of Example 95, the one or more branch anchor elements are configured to frictionally engage the branch member and the pump to anchor the pump within the branch member.

According to another example ("Example 109"), a system for implanting an implantable medical device for cardiac assistance includes a first catheter configured to deploy an implantable medical device within an aorta, the implantable medical device including a main body, the main body including a lumen operable to maintain fluid flow through the aorta, the main body including an access site in a sidewall of the main body providing access to the lumen of the main body; and a second catheter configured to deploy a branch member within the access site to fluidly connect with the lumen of the main body and including a pump configured to convey blood through the branch member and into the lumen of the main body.

According to another example ("Example 110"), further to the system of Example 109, the second catheter is configured to deploy the branch member transapically.

According to another example ("Example 111"), further to the system of Example 109, the second catheter is configured to deploy the branch member transseptally.

According to another example ("Example 112"), further to the system of any one of Examples 109-111, the system also includes a puncture device configured to create an access site in the aorta and an access site in an atrium or ventricle, and wherein the second catheter is configured to deploy the branch member across the access site in the aorta and the access site in an atrium or left ventricle.

According to another example ("Example 113"), further to the system of Example 112, the second catheter includes a sheath configured to deploy a flange arranged with a distal end of the branch member, the flange is configured to engage a tissue wall of the atrium or the ventricle in a fluid tight engagement.

According to one example ("Example 114"), an implantable medical device for cardiac assistance a pump configured to deploy within a pulmonary vein, the pump including a lumen configured to maintain blood flow through the pulmonary vein and configured to convey blood through the lumen.

According to another example ("Example 115"), further to the device of Example 114, the pump is configured to intake blood from the pulmonary vein and discharge the blood into the left atrium.

According to another example ("Example 116"), further to the device of any one of Examples 114-115, the pump is configured to increase flow out of the pulmonary vein to increase cardiac output.

According to another example ("Example 117"), further to the device of any one of Examples 114-117, the device also includes a driveline configured to power the pump, the driveline configured to extend out of the pulmonary vein into the left atrium and across a septum to exit a right side of the heart.

According to another example ("Example 118"), further to the device of Example 117, the driveline is operable to exit a patient via an iliac vein.

According to another example ("Example 119") a method for cardiac assistance including arranging an implantable medical device between an aorta and a heart chamber of a patient, the implantable medical device including a pump configured to convey blood from the heart chamber into the aorta; and forming a conduit of native tissue about the pump and between the aorta and the heart chamber.

According to another example ("Example 120"), further to the method of Example 119, forming the conduit of native tissue includes creating scarring or tissue ingrowth to form a tissue layer between the aorta and the heart chamber.

According to another example ("Example 121"), further to the method of any one of Examples 119-120, the pump includes a material arranged about an outer surface of the pump configured to facilitate tissue ingrowth.

According to another example ("Example 122"), further to the method of Example 121, the material includes at least one of Dacron and ePTFE.

According to one example ("Example 123"), a medical device for cardiac assistance includes a support frame, a plurality of leaflets coupled to the support frame and configured to open to allow forward flow therethrough and to occlude the support frame to prevent retrograde flow, and a pump arranged within the support frame and configured to convey blood through the support frame.

According to another example ("Example 124"), further to the device of Example 123, the plurality of leaflets are configured to coapt about the pump.

According to another example ("Example 125"), further to the device of Example 124, the pump is arranged centrally within the support frame.

According to another example ("Example 126"), further to the device of any one of Examples 123-125, the device also includes a filter arranged at an outflow end of the support frame.

According to another example ("Example 127"), further to the device of Example 126, the filter is arranged on an outflow end of the pump.

According to another example ("Example 128"), further to the device of any one of Examples 123-127, the prosthetic valve is configured to replace an aortic valve of a patient.

According to another example ("Example 129"), further to the device of any one of Examples 123-128, the prosthetic valve is configured to replace a mitral valve of a patient.

According to another example ("Example 130"), further to the device of any one of Examples 123-129, the prosthetic valve and the pump are configured for transcatheter delivery.

According to another example ("Example 131"), an implantable medical device for cardiac assistance include a main body configured to deploy within an aorta, the main body including a lumen configured to maintain fluid flow through the aorta; a branch member extending from the main body and configured to deploy within a chamber of a heart to fluidly connect the aorta and the chamber of the heart; and a pump arranged within the branch member and configured to convey blood from the chamber of the heart through the branch member and into the lumen of the main body.

According to another example ("Example 132"), further to the device of any Example 131, the branch member is integral with the main bod.

According to another example ("Example 133"), further to the device of Example 132, the branch member is configured to telescope inwardly and outwardly relative to the main body.

According to another example ("Example 134"), an implantable medical device for cardiac assistance includes a stent-graft configured to deploy within a pulmonary vein and including a lumen configured to maintain fluid flow through the pulmonary vein, the stent-graft configured to receive blood through the lumen.

According to another example ("Example 135"), further to the device of Example 134, the stent-graft configured to interface with a pump, and the pump configured to convey blood from the pulmonary vein to a left atrium.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

Figure 1:
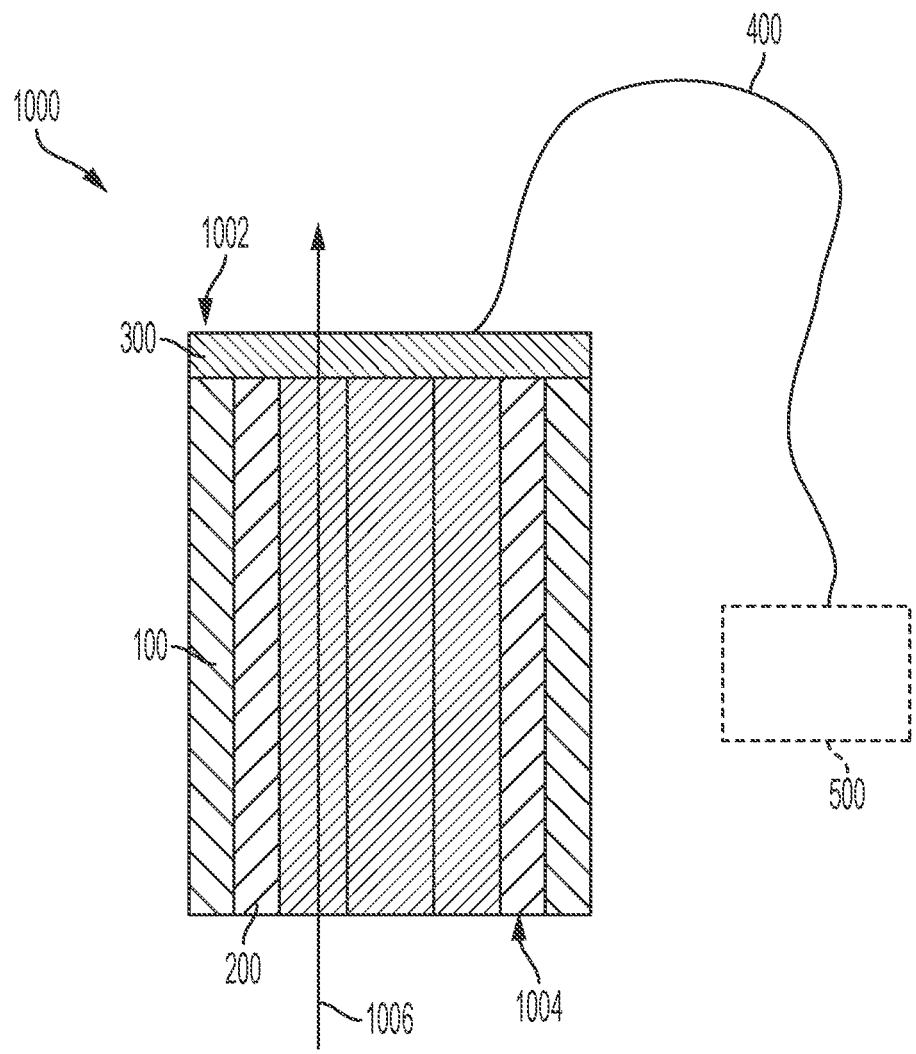
FIG. 1 is an illustration of a system including a branch member and a pump, according to some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Definitions and Terminology

As the terms are used herein with respect to ranges of measurements "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like. In the event it is determined that individuals having ordinary skill in the relevant arts would not readily ascertain values for such reasonably small differences, the terms "about" and "approximately" can be understood to mean plus or minus 10% of the stated value.

Certain terminology is used herein for convenience only. For example, words such as "top", "bottom", "upper," "lower," "left," "right," "horizontal," "vertical," "upward," and "downward" merely describe the configuration shown in the figures or the orientation of a part in the installed position. Indeed, the referenced components may be oriented in any direction. Similarly, throughout this disclosure, where a process or method is shown or described, the method may be performed in any order or simultaneously, unless it is clear from the context that the method depends on certain actions being performed first.

Description of Various Embodiments

Various aspects of the present disclosure are directed to systems and methods for improving or assisting the cardiac function of the heart. The disclosed systems and methods generally include an endoprosthesis having a pump within the patient's vasculature. The disclosed systems and methods also include a delivery system configured for transcatheter delivery of the pump and the branch member.

In the instant disclosure, the examples are primarily described in association with transcatheter cardiac applications involving the aorta (also referred to herein as ventricular assist), although it should be readily appreciated that the various embodiments and examples discussed herein can be applied in association with any known uses of ventricular assist devices, including for use within other regions of the heart or vasculature, as well as percutaneous procedures (e.g., laparoscopic) and/or surgical procedures. Cardiac assist devices, as discussed herein, may be beneficial for patients experiencing heart failure. The cardiac assist devices, consistent with various aspects of the present disclosure may include an implantable pump that forces or conveys blood from chambers of the heart (e.g., the right ventricle or left ventricle) to the rest of the body (e.g., via the aorta).

As shown in FIG. 1, a system 1000 according to various embodiments includes a branch member 100 and a pump 200 disposed at least partially within the branch member 100, and a retention element 300 configured to help maintain a position of the pump 200 within the branch member 100. The branch member 100 may be a branch member 100 that forms a part of a branched implantable medical device as discussed in further detail below.

In certain instances, the branch member 100 may include a graft, a stent, or a combination of a stent and a graft. As discussed in further detail below, the branch member 100 may be a stent-graft device that is incorporated with a stent-graft device implanted into a patient's aorta thereby forming a branched implantable medical device. The branch member 100 may be a branch member coupled or joined to a main stent-graft device that is implanted in the aorta. In certain instances, the branch member 100 and pump 200 may act as a right ventricular assist device and increase blood flow into the pulmonary veins or arteries. In these instances, the main body 208 may be placed in the pulmonary artery with the branch member 100 be arranged in the atrium or ventricular as discussed in detail herein In certain instances, the stent portion of a branch member 100 is defined by a plurality of interconnected strut elements. The stent portion of the branch member 100 may comprise, such as, but not limited to, elastically deformable metallic or polymeric biocompatible materials. The stent portion of the branch member 100 may comprise a shape-memory material, such as nitinol, a nickel-titanium alloy. Other materials suitable for the stent portion of the branch member 100 include, but are not limited to, other titanium alloys, stainless steel, cobalt-nickel alloy, polypropylene, acetyl homopolymer, acetyl copolymer, other alloys or polymers, or any other biocompatible (e.g., bio-absorbable) material having adequate physical and mechanical properties to function as the stent portion of the branch member 100, as described herein. The stent portion of the branch member 100 may therefore be self-expanding and/or may be balloon expandable. That is, in various examples, the branch member 100 may be transitionable between a collapsed delivery configuration and an expanded deployed configuration.

In certain instances, the branch member 100 may be a stent that is partially covered with a graft material. The graft material of the branch member 100 may further include a graft material disposed thereabout (e.g., such as about an interior of or an exterior of the branch member 100). In various embodiments, graft materials can include, for example, expanded polytetrafluoroethylene (ePTFE), polyester, polyurethane, fluoropolymers, such as perfluoroelastomers and the like, polytetrafluoroethylene, silicones, urethanes, ultra high molecular weight polyethylene, aram id fibers, and combinations thereof. Other embodiments for a graft member material can include high strength polymer fibers such as ultra-high molecular weight polyethylene fibers (e.g., Spectra®, Dyneema Purity®, etc.) or aramid fibers (e.g., Technora®, etc.). Some embodiments may comprise of a graft material only partially disposed about the branch member frame.

In certain instances, the system 1000 is configured such that the pump 200 can be removably coupled with the branch member 100. In some examples, the pump 200 is removably coupled with the branch member 100 after the branch member 100 has been delivered and deployed within the patient's vasculature (e.g., a branch member of an implantable medical device). According to some implementations, the pump 200 is removable from the patient's vasculature without also requiring removal of the branch member 100 (e.g., such that the pump 200 may be replaced and/or such that removal of the system 1000 may be done minimally invasively).

The pump 200 is generally configured to drive or otherwise cause blood to flow across the pump 200 from an inflow side 1004 of the system 1000 to an outflow side 1002 of the system, such as along a direction of arrow 1006. The pump mechanism (also referred to herein as a pump drive) of the pump 200 may be, for example, a centrifugal-action pump, an axial-action pump, or other similar device such as a worm-style drive mechanism, or impeller. The pump housing is configured to interface and engage with the branch member 100. The pump 200 is situated within the deployed branch member 100 such that the pump 200 is operable to pump or drive blood across the pump 200 and into the aorta and out into the vasculature of the body. The pump 200 can be operated to draw blood from the left ventricle (or other heart chamber), blood across the pump 200, and into the aorta and out through the vasculature of the body.

In certain instances, the system 1000 further includes a driveline 400. The driveline 400 is a cable assembly that operates to electrically couple a controller 500 located external to the patient's anatomy with the pump 200 or the driveline 400 can be a rotating driveshaft. The driveline 400 may be routed through the patient's vasculature (e.g., exiting the heart through the apex of the left ventricle) and then out through the skin to where it is coupled with the controller 500 or to a subcutaneously implanted controller 500. The controller 500 is a module that is configured to control the operation of the pump 200. The controller 500 may include a batter to control operation of the pump 200.

In certain instances, the driveline 400 may be routed through one of the left or right subclavian arteries, veins, or the left common carotid artery to a subclavian or other associated access. Alternatively, the driveline 400 may be routed through the descending aorta to a femoral or other associated access. In certain instances, the driveline 400 is associated with the retention element 300, for example being routed through the retention element 300 or integral to the retention element 300. In some examples where the driveline 400 is integral with the retention element 300, the retention element 300 includes one or more connectors such that when the retention element 300 is coupled to the branch member 100, the driveline 400 is electrically coupled with the pump 200.

In some embodiments, the system 1000 may be configured to operate without the need for the driveline 400, or the driveline 400 need not extend extracorporeally. That is, in some examples, an extracorporeal control system may be configured to both control the operation of the pump, and to power the pump wirelessly (e.g., through a transcutaneous energy transmission system). In some examples, transcutaneous energy transmission may be accomplished through known means of transcutaneous energy transmission, such as those described in U.S. Pat. No. 6,400,991. Such a configuration eliminates the need to route the driveline 400 through the vasculature and out through a percutaneous access site, which can help minimize a risk for infection. In instances where the system 1000 is arranged trans-apically, the driveline 400 may not exit the patient through the thoracic cavity. In some examples, the driveline 400 may be configured to be unplugged or decoupled from the pump 200 at its junction with the pump 200. In some examples, decoupling the driveline 400 from the pump 200 includes decoupling or removing the retention element 300. In some examples, the system 1000 may include an "antenna" (or internal coil) that is configured for transcutaneous energy transfer ("TET"). In some examples, an extracorporeal TET component maybe worn around the torso similar to a standard heart rate monitor, and additionally coupled to a power source (wall unit or high capacity battery) such that the extracorporeal TET component is operable to transmit energy transcutaneously to the antenna.

As noted above, system 1000 may be incorporated into a branch member configured to interface with an access site of a main body of an implantable medical device. The main body and branch member (include the system 1000) may be compacted or collapsed to the delivery state prior to deployment with the main body of the implantable medical device as shown in further detail below.

Figure 2:
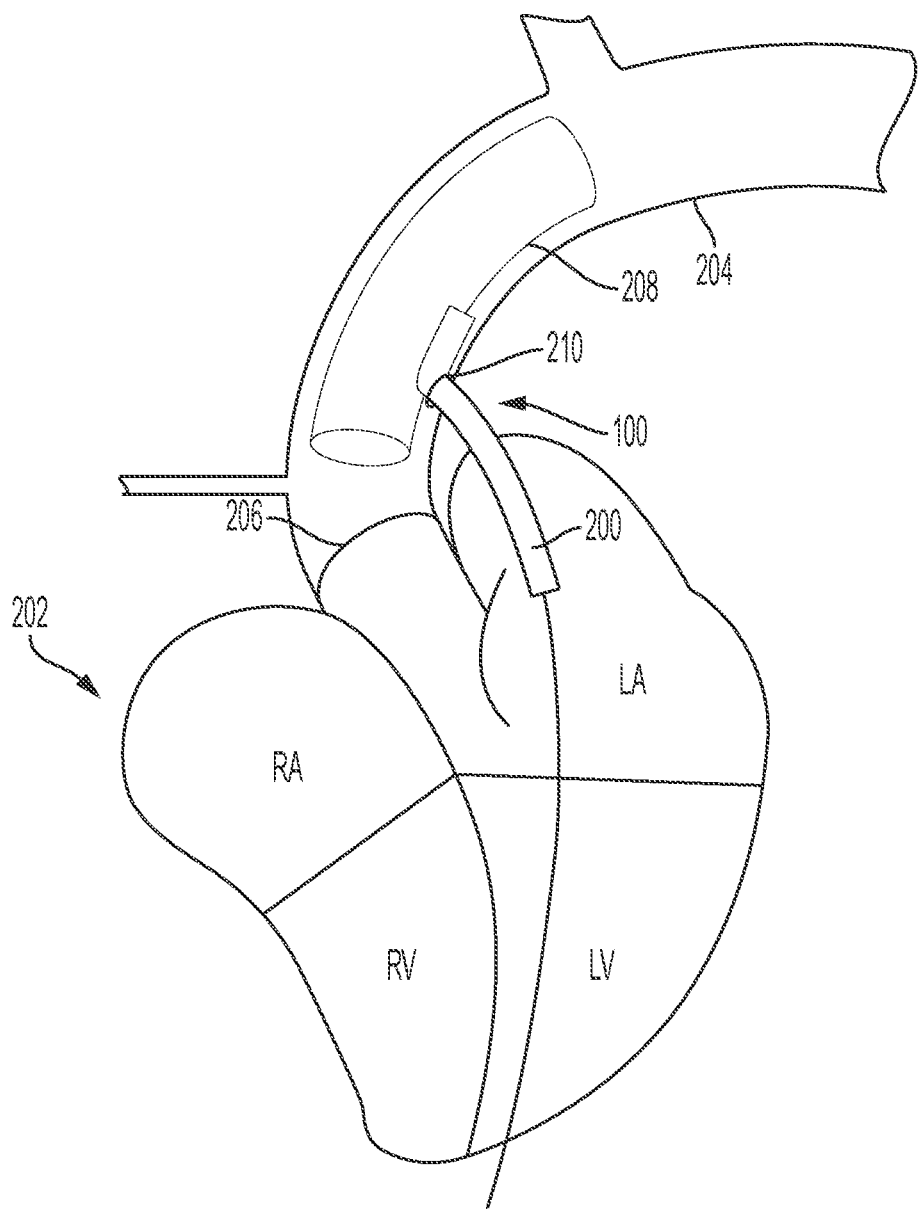
FIG. 2 is an illustration of an implantable medical device for cardiac assistance, according to some embodiments.

The system 1000 may be used as an implantable medical device for cardiac assistance as shown in FIG. 2. The system 1000 may be included with a main body 208 portion of an implantable medical device or with a branch member 100 that is coupled or joined to the main body 208 as discussed in further detail below. The implantable medical device is shown implanted in a patient's aorta 204 leading from a patient's heart 202. The patient's heart 202 is a simplified diagram and includes the aortic valve 206, the right atrium (RA), left atrium (LA), right ventricle (RV), and left ventricle (LV).

In certain instances, the implantable medical device includes a main body 208 configured to deploy within the aorta 204. The main body 208 includes a lumen maintaining fluid flow through the aorta 204. In addition, the main body 208 also includes an access site 210 in a sidewall of the main body 208 providing access to the lumen of the main body 208. The access site 210 may be a fenestration created before or after implantation of the main body 208. In addition, the main body 208 may include radiopaque markers arranged near adjacent the access site 210 to facilitate deployment. Further, the access site 210 may be deployed as facing away from the brachiocephalic, subclavian, and carotid arteries. The main body 208 may include a curvature or conform to a curvature of the aorta with the access site 210 being arranged opposite the curvature and thus be arranged as facing away from the brachiocephalic, subclavian, and carotid arteries.

The implantable medical device may also include a branch member 100 configured to deploy within the access site 210 to fluidly connect with the lumen of the main body 208. The branch member 100 may include a pump 200 configured to convey (or force) blood flow through the branch member 100 and into the lumen of the main body 208. The branch member 100 and pump 200 may include the structural and functional components described above with reference to system 1000. In addition and as noted above, the pump 200 may be configured to increase blood flow into the aorta 204 for cardiac assistance. In certain instances, the pump 200 may be integrated into the main body 208. In these instances, the main body 208 may lack an access site 210 and the pump 200 may increase blood flow within the aorta 204.

As shown in FIG. 2, the branch member 100 extends between the aorta 204 and the LA (e.g., forming an anastomosis between the two structures). In certain instances, the branch member 100 may be configured to implant within the RA or LV and connect to the main body 208 in the aorta 204. Implanting the branch member 100 in the LA may facilitate heart failure patients having preserved ejection fraction. The branch member 100 and main body 208 may function as a cardiac assist device with the pump 200 forcing blood from one or more chambers of the heart into the aorta 204. The branch member 100, main body 208, and pump 200 may be used to assist heart function for patients' having weakened hearts or heart failure.

As noted above, to facilitate coupling of the branch member 100 and the main body 208, the access site 210 of the main body 208 fluidly connects with the lumen of the main body 208. The access site 210 in the main body 208 may include a fenestration or a portal as discussed in further detail below with reference to FIG. 4 and FIG. 5. To deliver the branch member 100 and connect the aorta 204 and the LA, a puncturing device (e.g., arranged through the access site 210) creates a small access site in a tissue wall of the aorta 204 and the LA. The branch member 100, for example, may include stent-and graft components (as noted above with reference to FIG. 1) that allow for flexibility and relative motion between the aorta 204 and the LA (or LV). In certain instances, the branch member 100 is configured to couple the atrium (LA OR RA) and the aorta 2014 and allow independent motion of the atrium (LA OR RA) and the aorta 204.

In addition, the branch member 100 and pump 200 combination provides direct increase of blood flow for cardiac assistance. Further, the branch member 100 and pump 200 preserves space within the LA (or LV) to facilitate natural pumping of the heart 202, avoid interfering with valves of the heart 202, and enable transcatheter implantation. The pump 200 may be configured to deliver the blood flow through the branch member 100 and into the lumen of the main body 208 parallel to natural blood flow through the aorta 204. As discussed in further detail below, the branch member 100 and pump 200 may be collapsed to a delivery configuration of transcatheter delivery. Having the main body 208 arranged in the aorta 204 mitigates the risk of aortic dissection, protects the aortic wall from an increased fluid flow from the pump 200, and may reduce risk of device deployment.

In addition and as noted above with reference to FIG. 1, the pump 200 may be removably coupled to the branch member 100. The pump 200 may be delivered with the branch member 100 or delivered separately after the branch member 100 is fluidically coupled to the main body 208. The pump 200 may anchor within the branch member 100. The pump 200, for example, may have retractable anchors that extend after the pump 200 is forced from a delivery sheath as shown in further detail with reference to FIG. 9. In the event that the pump 200 is replaced or removed, the anchors may retract inwardly from the branch member 100 as the branch member 100 is withdrawn into the delivery sheath. The branch member 100 may have a collar or that interfaces with the pump 200. In other instances, the pump 200 and the branch member 100 may be correspondingly keyed to fix the pump 200 and the branch member 100. The keying may occur by rotation of the pump 200 within a deployed branch member 100.

As noted above, the main body 208 may be arranged within the aorta 204 and more specifically the ascending aorta. The main body 208 may protect the aorta 204 from the pump 200 shifting or shearing. In addition, the main body 208 may minimize tissue overgrowth near the pump 200 outlet and facilitate retrieval of the pump 200.

Figure 3A:
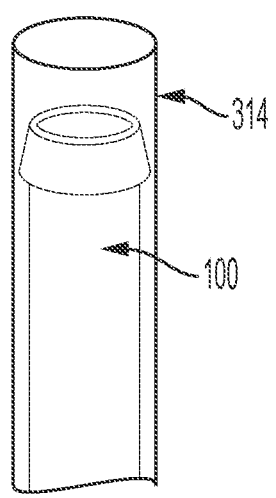
FIG. 3A is an illustration of a delivery sheath and a branch member of an implantable medical device for cardiac assistance in a first configuration, according to some embodiments.

FIG. 3A is an illustration of a delivery sheath 314 and a branch member 100 of an implantable medical device for cardiac assistance in a first configuration, according to some embodiments. The delivery sheath 314 may be used to facilitate delivery (e.g., along with a guidewire and/or delivery catheter) of the branch member 100 to connect the aorta and the left atrium (or left ventricle). As shown in FIG. 3A, the branch member 100 is collapsed or constrained within the delivery sheath 314. The branch member 100 may include a sealing element 316 near or at an end of the branch member 100 that is configured to engage a tissue wall of the atrium or the left ventricle.

Figure 3B:
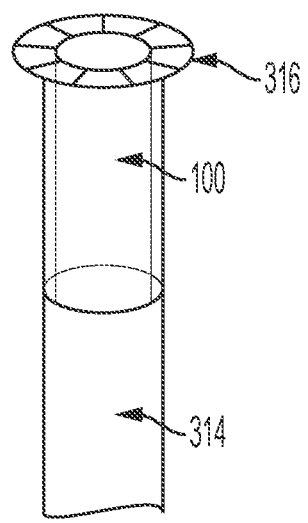
FIG. 3B is an illustration of the delivery sheath and the branch member, shown in FIG. 3A, in a second configuration, according to some embodiments.

As shown in FIG. 3B, the sealing element 316 deploys when the branch member 100 is deployed from the delivery sheath 314. The sealing element 316 may be collapsed against an exterior surface of the branch member 100 in the delivery sheath 314 and extend outwardly after the branch member 100 is deployed. In certain instances, the sealing element 316 may be arranged on both ends of the branch member 100 with one of the sealing elements 316 being configured to dock and seal the branch member 100 within a fenestration of a main body (as shown above with reference to FIG. 2) and the other of the sealing elements 316 being configured to arrange and secure the branch member 100 to a tissue wall of the heart.

Figure 4:
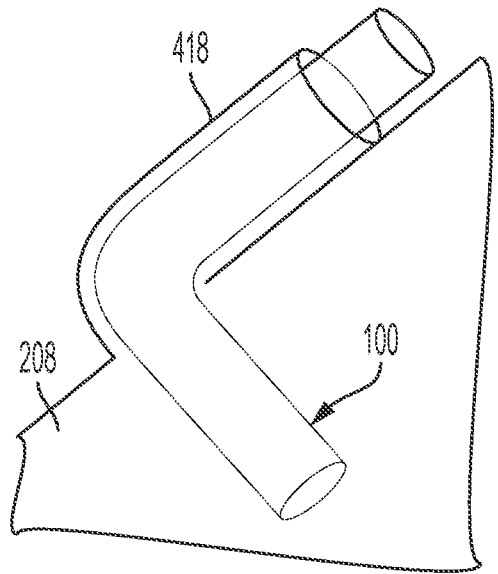
FIG. 4 is an illustration of a branch member of an implantable medical device arranged within a portal, according to some embodiments.

FIG. 4 is an illustration of a branch member 100 of an implantable medical device arranged within a portal 418, according to some embodiments. The portal 418 may be arranged within a main body 208 of an implantable medical device for ventricular assist (e.g., as shown in FIG. 2). The portal 418 may be aligned with an access site 210 in the main body 208 and the branch member 100 may be configured to implant within the portal 418 to fluidly connect the branch member 100 and the main body 208.

In certain instances, portal 418 includes a support wall and secondary lumen having a first longitudinal orientation will therefore define a blood flow direction of the branch member 100 that is aligned with the blood flow direction of the main body 208. The support wall of the portal 418 may include a stent and a graft component. Further details on internal support walls for supporting branch members extending through access sites in the main body are disclosed in U.S. Pat. No. 6,645,242 to Quinn.

Figure 5:
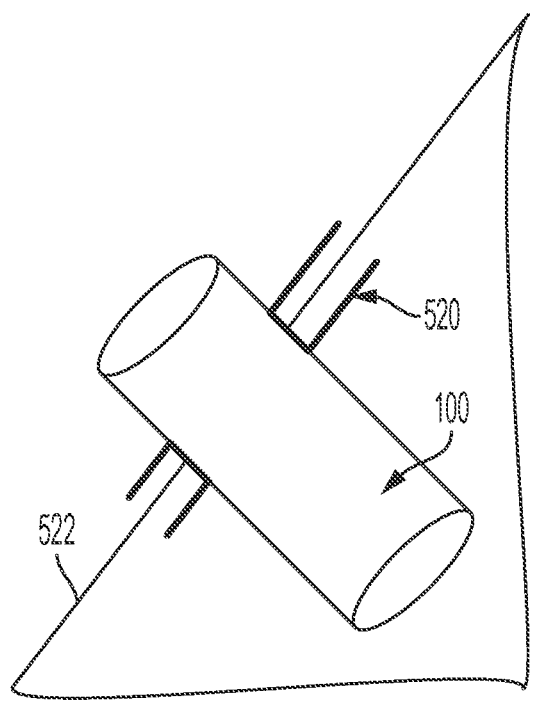
FIG. 5 is an illustration of a branch member and flange, according to some embodiments.

FIG. 5 is an illustration of a branch member 100 and flange 520, according to some embodiments. The flange 520 may be configured to engage a tissue wall 522 in a fluid tight fluid engagement between the branch member 100 and atrium or ventricle into which the branch member 100 is arranged. The flange 520 prevents leakage between the puncture made in the atrium or ventricle and the branch member 100.

The flange 520 may be integrated with the branch member 100 or separately deployed and anchored with the branch member 100. In certain instances, the flange 520 may be balloon expandable to deploy about the tissue wall 522. The flange 520 may extend and flatten out around the tissue wall 522 after balloon or self-expansion after deployment from a delivery sheath 314 as discussed in detail above. The flange 520 may include a stent and/or a graft portion or may include a polymeric material.

Figure 6:
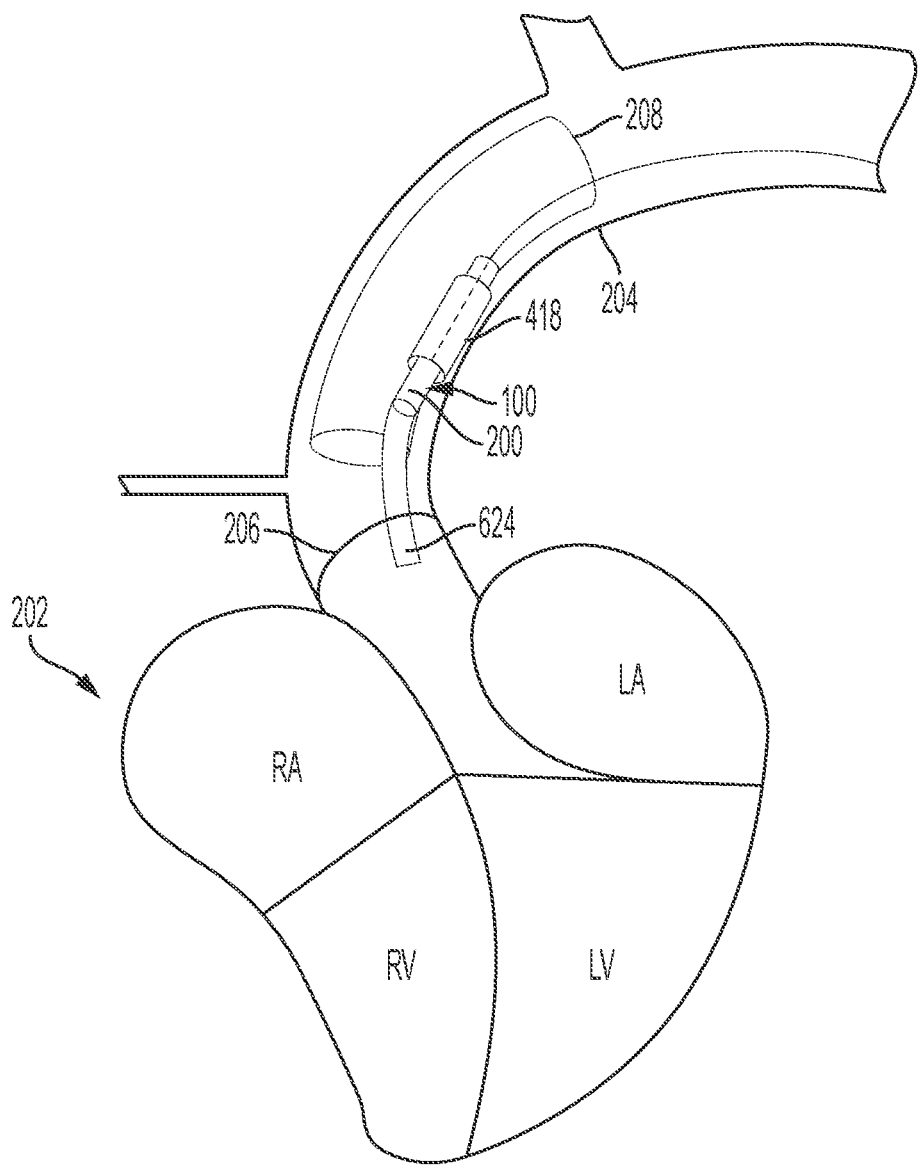
FIG. 6 is an illustration of another implantable medical device for cardiac assistance, according to some embodiments.

FIG. 6 is an illustration of another implantable medical device for cardiac assistance, according to some embodiments. The implantable medical device is shown implanted in a patient's aorta 204 leading from a patient's heart 202. The patient's heart 202 is a simplified diagram and includes the aortic valve 206, the right atrium (RA), left atrium (LA), right ventricle (RV), and left ventricle (LV).

In certain instances, the implantable medical device includes a main body 208 configured to deploy within the aorta 204. The main body 208 includes a lumen maintaining fluid flow through the aorta 204. In addition, the main body 208 also includes a portal 418 coupled to the main body 208 providing access to the lumen of the main body 208. The implantable medical device may also include a branch member 100 configured to deploy within the portal 418 to fluidly connect with the lumen of the main body 208. The branch member 100 may include a pump 200 configured to convey blood through the branch member 100 and into the lumen of the main body 208. The branch member 100 and pump 200 may include the structural and functional components described above with reference to system 1000. In addition and as noted above, the pump 200 is configured to increase blood flow into the aorta 204 for cardiac assistance. In certain instances, the pump 200 may be integrated into the main body 208. In these instances, the main body 208 may lack an access site 210 and the pump 200 may increase blood flow within the aorta 204.

In addition, the branch member 100 may be configured to be disposed within the aorta adjacent or across the aortic valve 208 or between leaflets of the valve 206. The branch member 100 may be configured to allow the aortic valve 208 to close about the branch member 100 to avoid backflow or leakage while utilized the pump 200 may increase blood flow within the aorta 204. In certain instances, the branch member 100 includes a cannula 624 that extends from end of the branch member 100 with the cannula 624 being arranged within the aortic valve 208.

Figure 7:
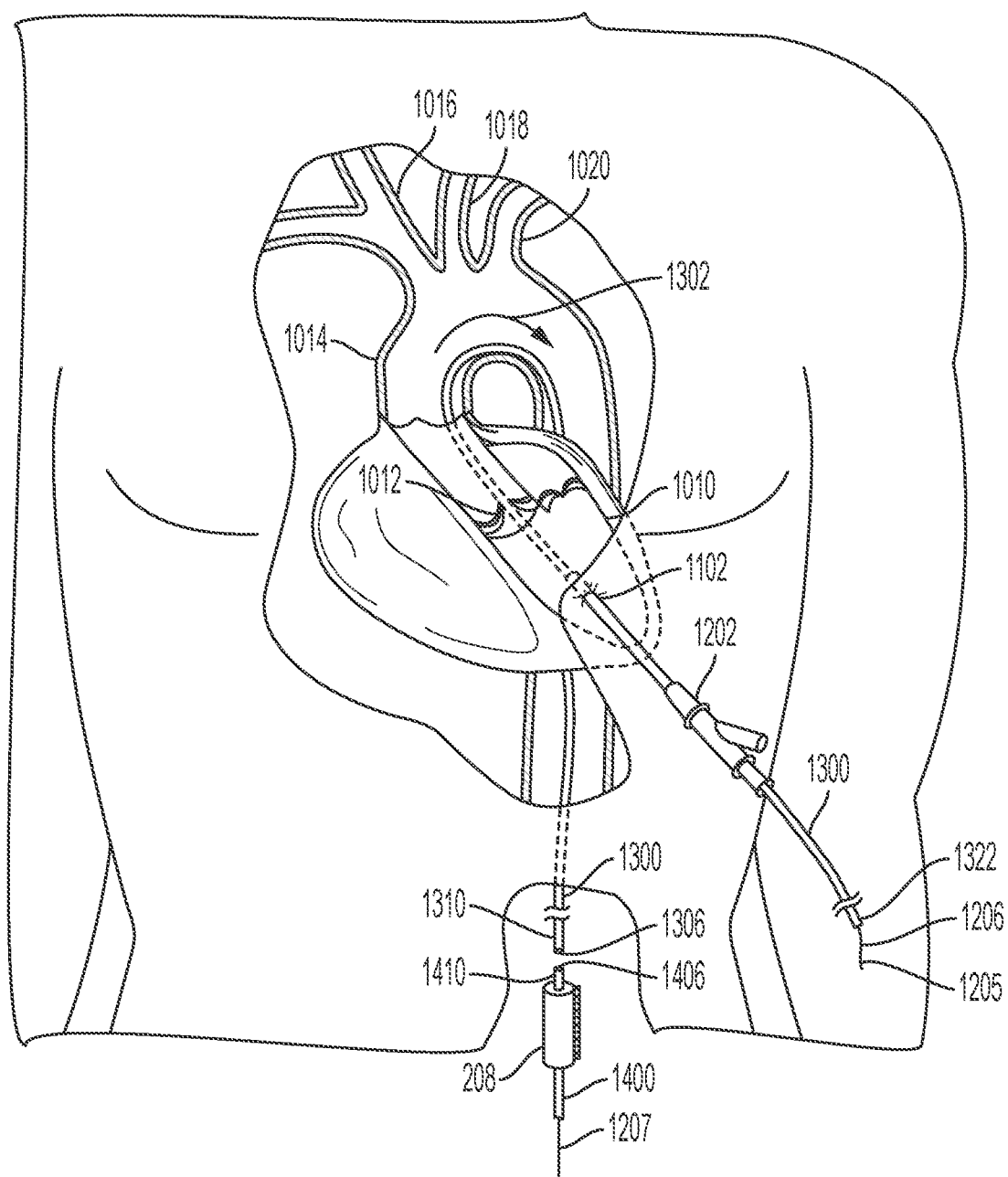
FIG. 7 is an illustration of an example delivery system for an implantable medical device for cardiac assistance, according to some embodiments.

FIG. 7 is an illustration of an example delivery system for an implantable medical device for cardiac assistance, according to some embodiments. The delivery system is shown utilizing both trans-apical access and trans-femoral access sites, which allows delivery of an implantable medical device with a branch member inside of the heart through manipulation of at least two portions or members of the delivery system from outside of the body from the respective trans-apical and trans-femoral access sites. As discussed in further detail below, the delivery system of the present disclosure is transcatheter-based and avoids open heart surgery that may be required for prior cardiac assistance devices.

Figure 10:
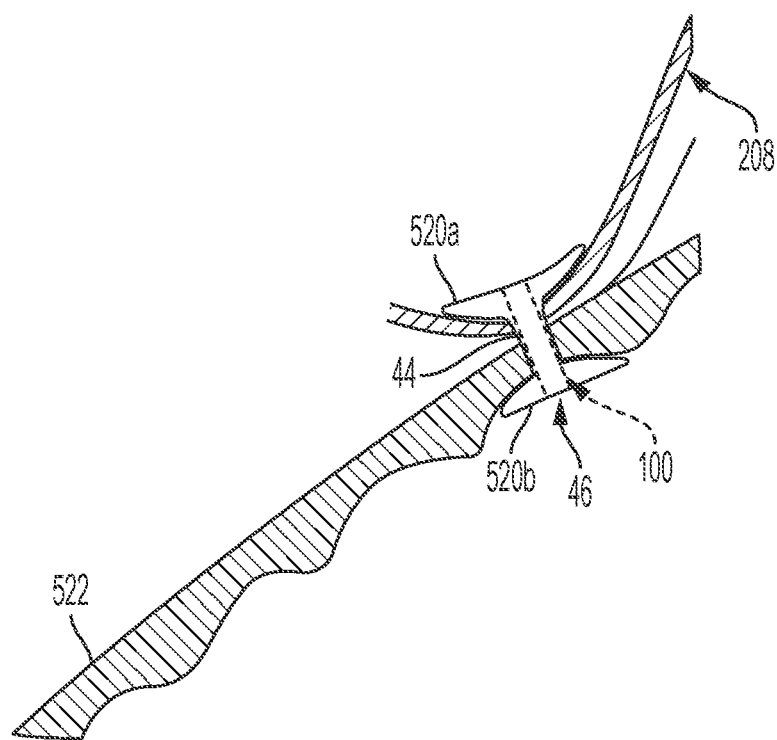
FIG. 10 is an illustration of an example branch member with flanges, according to some embodiments.

The delivery system can, for example, be used to deploy an implantable medical device, such as a main body 208 for placement in the ascending portion of the aortic. A guidewire 1206 can be inserted through the trans-apical access site and into the left ventricle 1010 of the heart 1100, as shown in FIG. 10. The guidewire 1206 can be routed through the aortic valve 1012, the aorta 1014, a femoral artery of one of the legs, and out of the body via the trans-femoral access site (not shown), resulting in a "body floss" or "through-and-through" access configuration, wherein opposite terminal ends 1205, 1207 of the guidewire 1206 extend outside of the body from respective trans-apical and trans-femoral access sites 1102, 1104.

A first catheter, generally indicated at 1300, includes a leading end 1306 and an opposite trailing end 1322. The first catheter 1300 has a guidewire lumen 1310 through which the guidewire 1206 can be routed. A first end 1205 of the guidewire 1206 can be inserted into the guidewire lumen 1310 at the leading end 1306 of the first catheter 1300. The leading end 1306 of the first catheter 1300 can be fed into the vasculature through the trans-apical access site 1102 via the first introducer sheath 1202. The first catheter 1300 can then be pushed along the guidewire 1206 in the direction indicated at 1302 until the leading end 1306 exits the trans-femoral access site (not illustrated). The trailing end 1322 of the first catheter 1300 remains outside of the body and extends from the first access site 1102 via the first introducer sheath 1202. In this configuration, the catheter 1300 can be maneuvered by pushing or pulling the leading end 1306 and the trailing end 1322 of the first catheter 1300 from outside of the body.

A second catheter, generally indicated at 1400, includes a leading end 1406 and an opposite trailing end 1422. The second catheter 1400 has a guidewire lumen 1410 for receiving the guidewire 1206 therethrough. The second end 1207 of the guidewire 1206 can be inserted into the guidewire lumen 1410 at the leading end 1406 of the second catheter 1400. The second catheter 1400 can be pushed along the guidewire 1206 until the leading ends 306, 306 engage. Although shown with guidewires 1206, the catheters 1300, 1400 may be used within guidewires 1206 in certain instances.

The leading ends 1306, 1406 of the first and second catheters 1300, 1400 can be configured for matingly engaging or coupling to each other. Further, the leading ends 1306, 1406 can be configured for releasably coupling to each other. The leading ends 1306, 1406 of the first and second catheters 1300, 1400 can be coupled to each other extra corporeal or in situ. Once the leading ends 1306, 1406 are coupled, the trailing ends 1322, 1422 of the first and second catheters 1300, 1400 can be accessed outside of the body from the respective trans-apical access site 1102 and trans-femoral access site 1104 and pushed, pulled and rotated to axially and rotatably position a main body portion 208 of the implantable medical device at the treatment site.

The main body portion 208 can be releasably maintained or radially compressed toward a delivery configuration for endoluminal delivery by any suitable constraining means, such as a film constraining sleeve, a constraining tether or lattice, retractable sheath and the like as shown in FIG. 7. Optionally, one or more constraining means or combination of constraining means can be configured to allow staged expansion through one or more intermediate expanded states leading to full deployment. The branch member 100 (not shown) may be similarly constrained.

Other surgical tools may be delivered through a third access point to the aorta through one of the major branch arteries along the aorta in connection with the deployment of the device at or in the heart or along the aorta. For example, a filter may be deployed to filter blood entering the branch arteries 1016, 1018, 1020.

The catheters 1300,1400 may also deliver the main body 208 and the branch member 100 from femoral vein with trans-septal puncture or from apex of heart (trans apical puncture and through mitral up through aorta) or on the ventricle side as well. In certain instances, the main body 208 is delivery through the femoral artery and the branch is delivery from the femoral artery or vein.

In delivery the branch member 100 across the aorta 1014 and into the atrium or ventricle, one or both of the catheters 1300,1400 may include a puncturing device that creates access sites in the tissue wall of the aorta 1014 and the atrium or ventricle. In addition, one or both of the catheters 1300,1400 may include a delivery sheath (as noted above) that is pressed against the tissue when and after the access sites are created. Magnets or other coupling members in the delivery sheaths of the catheters 1300,1400 may attach together for deployment of the branch member 100.

The catheters 1300,1400 may be used to deploy the main body 208 in the aorta 1014 and the branch member 100 across the aorta 1014 and into the atrium or ventricle. More specifically, the first catheter 1300 may deploy the main body 208 and the second catheter 1400 may deploy the branch member 100. In other instances, the main body 208 can be deployed in the aorta 1014 and the branch member 100 can be deployed across the aorta 1014 and into the atrium or ventricle by using one of the catheters 1300, 1400 with a trans-septal approach (across atrial septum into the left atrium) and the other of the catheters 1300, 1400 using a femoral approach.

Figure 8A:
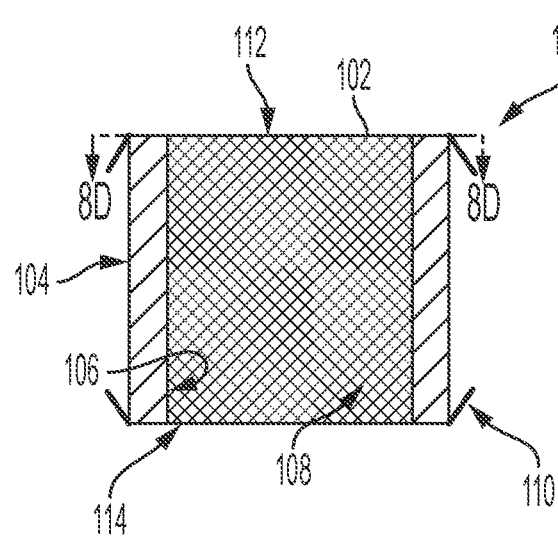
FIG. 8A is an illustration of a branch member according to some embodiments.
Figure 8B:
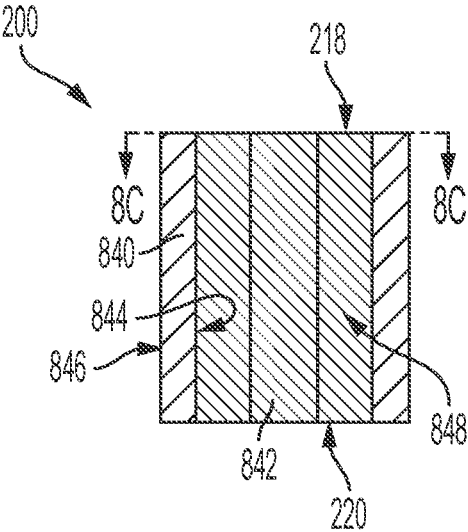
FIG. 8B is an illustration of a pump, according to some embodiments.
Figure 8C:
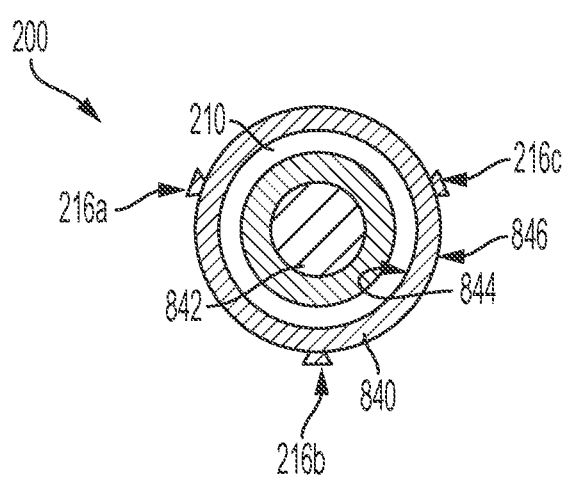
FIG. 8C is a cross sectional view of the branch member shown in FIG. 8C, taken along line 8A-8A.
Figure 8D:
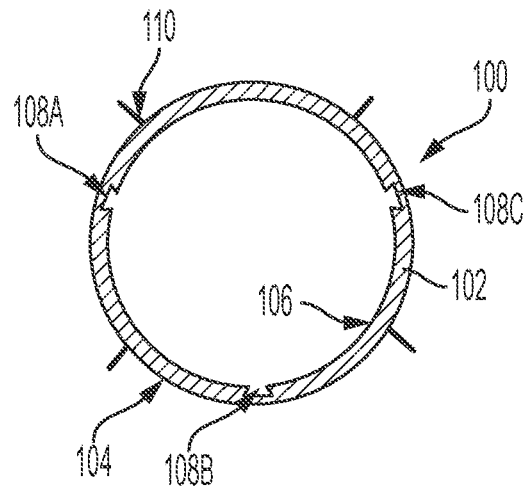
FIG. 8D is a cross sectional view of the pump shown in FIG. 8B, taken along line 8B-8B.

FIG. 8A is an illustration of a branch member according to some embodiments. FIG. 8B is an illustration of a pump, according to some embodiments. FIG. 8C is a cross sectional view of the branch member shown in FIG. 8C, taken along line 8A-8A. FIG. 8D is a cross sectional view of the pump shown in FIG. 8B, taken along line 8B-8B.

With reference now to FIG. 8A, the branch member 100 generally includes a stent body 102 defining an exterior 104 and an interior 106. The stent body 102 may be generally cylindrically shaped and configured to adopt a profile consistent with the vasculature within which is it deployed and expanded. In some examples, the stent body 102 is defined by a plurality of interconnected strut elements 108 or helically wound strut elements 108.

For example, as shown in FIG. 8B, the pump 200, arranged within at least a portion of the branch member 100 or extending from the branch member 100, generally includes a pump housing 840 and a pump drive element 212. The pump housing 840 generally defines an exterior 846 and an interior 844. The exterior 846 of the pump housing 840 is configured to engage and interface with the interior 106 of the branch member 100 such that the pump 200 can be coupled with the branch member 100. The interior 844 of the pump housing 840 is configured to house or accommodate the pump drive element 212 such that the pump drive element 212 can move relative to the pump housing 840 to cause blood to flow through the pump 200. In some examples, blood travels through the pump 200 within an annular space 848 that is defined between the pump drive element 212 and the pump housing 840, although other pump configurations are contemplated and fall within the scope of the present disclosure provided that the pump housing can be configured to interface and engage with the branch member 100. Thus, although the pump drive element 212 shown in FIG. 8B includes a worm drive having a helical flange extending about a central shaft (e.g., an impeller configuration), the application should not be understood to be limited to such configuration, but should instead be understood to be operable with other pump drive configurations.

As mentioned above, in various embodiments, the pump 200 is receivable within the branch member 100. As shown in FIGS. 8C and 8D, the each of the pump 200 and the branch member 100 include complementary features that facilitate the coupling of the branch member 100 with the pump 200.

As shown in FIG. 8C, the branch member 100 includes a plurality of pump locating features 108a, 108b, and 108c. In this illustrated example, the pump locating features 108a-108c are channels or recesses that extend longitudinally along a longitudinal axis of the branch member 100. In some examples, the pump locating features 108a-108c extend parallel to the longitudinal axis of the branch member 100. In some examples, one or more of the pump locating features 108a-108c extend along less than all of the length of the branch member 100. That is, in some examples, the pump locating features 108a-108c extend only partially between the first end 112 and the second end 114 of the branch member 100. In some such examples, one or more of the pump locating features 108a-108c terminates at a location between the first and second ends 112 and 114. This termination of the one or more channels or recesses of the pump locating features 108a-108c operates as an abutment against which the pump housing 840 of the pump 200 can sit.

As explained further below, such a configuration provides that the pump housing 840 of the pump 200 may only be inserted into and removed from the branch member 100 in a unidirectional manner. For instance, when inserted into the branch member 100, the pump 200 can be advance longitudinally along the branch member 100 until the pump housing 840 engages the termination point of the one or more channels or recesses of the pump locating features 108a-108c. Moreover, when being removed from the branch member 100, the pump 200 can only be withdrawn in a direction opposite from that direction in which the pump 200 was advanced when it was coupled to the branch member 100. Securing the pump 200 within the branch member 100 in such a manner operates to prevent the pump 200 from being drawn through the branch member 100.

As mentioned above, the pump housing 840 generally includes one or more features that are complimentary of the pump locating features 108a-108c of the branch member 100. With reference now to FIG. 8D, the pump housing 840 is shown as including a plurality of stent engagement elements 216a, 216b, and 216c. As shown, the stent engagement elements 216a-216c are features that protrude from the exterior of the pump housing 840. The stent engagement elements 216a-216c extend longitudinally along the exterior 846 of the pump housing 840, such as parallel to a longitudinal axis of the pump housing 840. In some examples, the stent engagement elements 216a-216c extend between the first end 218 and the second end 220 of the pump housing 840. In some examples, one or more of the stent engagement elements 216a-216c may extend beyond (or alternatively short of) one or more of the first and second ends 218 and 220 of the pump housing 840. The stent engagement elements 216a-216c are generally complimentary in shape, size, and location and orientation of the pump locating features 108a-108c such that the stent engagement elements 216a-216c can be received within the pump locating features 108a-108c.

As shown in FIGS. 8C and 8D, the stent engagement elements 216a-216c are formed as positive dovetail features while the pump locating features 108a-108c are formed as the complimentary negative dovetail features. Additionally, the stent engagement elements 216a-216c are shown as being evenly distributed circumferentially about the exterior 846 of the pump housing 840, while the pump locating features 108a-108c are similarly evenly distributed circumferentially about the interior 106 of the branch member 100.

It is to be appreciated that the interaction between the stent engagement elements 216a-216c and the pump locating features 108a-108c operates to help locate the pump 200 within the branch member 100. For instance, the engagement between stent engagement elements 216a-216c and the pump locating features 108a-108c (the combination of which are referred to herein as alignment features) helps to align the pump 200 longitudinally with respect to the branch member 100. Likewise, the engagement between stent engagement elements 216a-216c and the pump locating features 108a-108c helps to align the pump 200 coaxially with the branch member 100.

Additionally, in various examples, this interaction also operates to prevent pitch/yaw/roll (e.g., rotation relative to the longitudinal axis of the branch member 100) of the pump housing 840 relative to the branch member 100 during operation of the system 1000, which provides the constraint necessary to allow the pump 200 to operate to drive blood flow across the pump 200 (e.g., the pump drive element 212 can rotate or be rotated relative to the pump housing 840 without the pump housing 840 also rotating).

In various examples, with the pump 200 properly aligned and seated within the branch member 100, the pump housing 840 and the branch member 100 form a seal therebetween such that blood cannot flow between the pump housing 840 and the branch member 100. In some examples, the pump housing 840 is suspended within the branch member 100 such that blood can flow either through/across the pump drive element 842, or around the pump housing 840. Such a configuration allows for blood flow around the pump in the case of a pump failure, and additionally provides favorable hemodynamics with regard to hem olysis and perfusion of the coronary arteries. In some examples, bypass blood flow (e.g., blood flow around the pump 200 may be facilitated by the branch member 100, itself. For instance, in some examples, the branch member 100 may include an open celled stent structure, wherein the pump 200 is positioned within or suspended by the open celled stent branch member, which allows for blood to flow through and around the pump 200 (e.g., through the open cells of the stent branch member.

It is also to be appreciated that while the branch member 100 and the pump 200 shown in FIGS. 8C and 8D include complementary alignment features that are in the shape of dovetails, various other sizes and shapes of such features are envisioned and can be implemented without departing from the spirit or scope of the present disclosure. For example, the dovetail geometry may be replaced with one or more of various alternative geometries, including but not limited to, triangles, squares, and polygons. Similarly, though the FIGS. 8C and 8D show three evenly distributed (e.g., positioned 120 degrees away from each other) alignment features (e.g., stent engagement elements 216a-216c and pump locating features 108a-108c), as little as one or two such alignment features may be used, or more than three such alignment features may be used. Likewise, where more than one alignment feature is used, such alignment features need not be evenly distributed about the interior/exterior of the branch member 100 and the pump housing 840.

It should also be appreciated that while the alignment features shown in FIGS. 8C and 8D extend longitudinally along the branch member 100 and the pump housing 840, the alignment features may alternatively be arranged in a helical pattern. In such an alternative configuration, the pump 200 is coupleable with the branch member 100 by aligning the helical alignment features of the pump 200 and the branch member 100 with one another and then rotating the pump 200 and the branch member 100 relative to one another, such as about the longitudinal axis of the branch member 100, for example.

It should also be appreciated that while the branch member 100 and the pump 200 shown in FIGS. 8C and 8D are shown with the alignment features protruding from the exterior 846 of the pump housing 840 and as channels or recesses along the interior 106 of the branch member 100, in some other examples, the alignment features may protrude from the interior 106 of the branch member 100 and be formed as recesses or channels along the exterior 846 of the pump housing 840. Alternatively, the branch member 100 and the pump housing 840 may each include a combination of alignment features that protrude therefrom and that are formed as recesses or channels therein.

Figure 9:
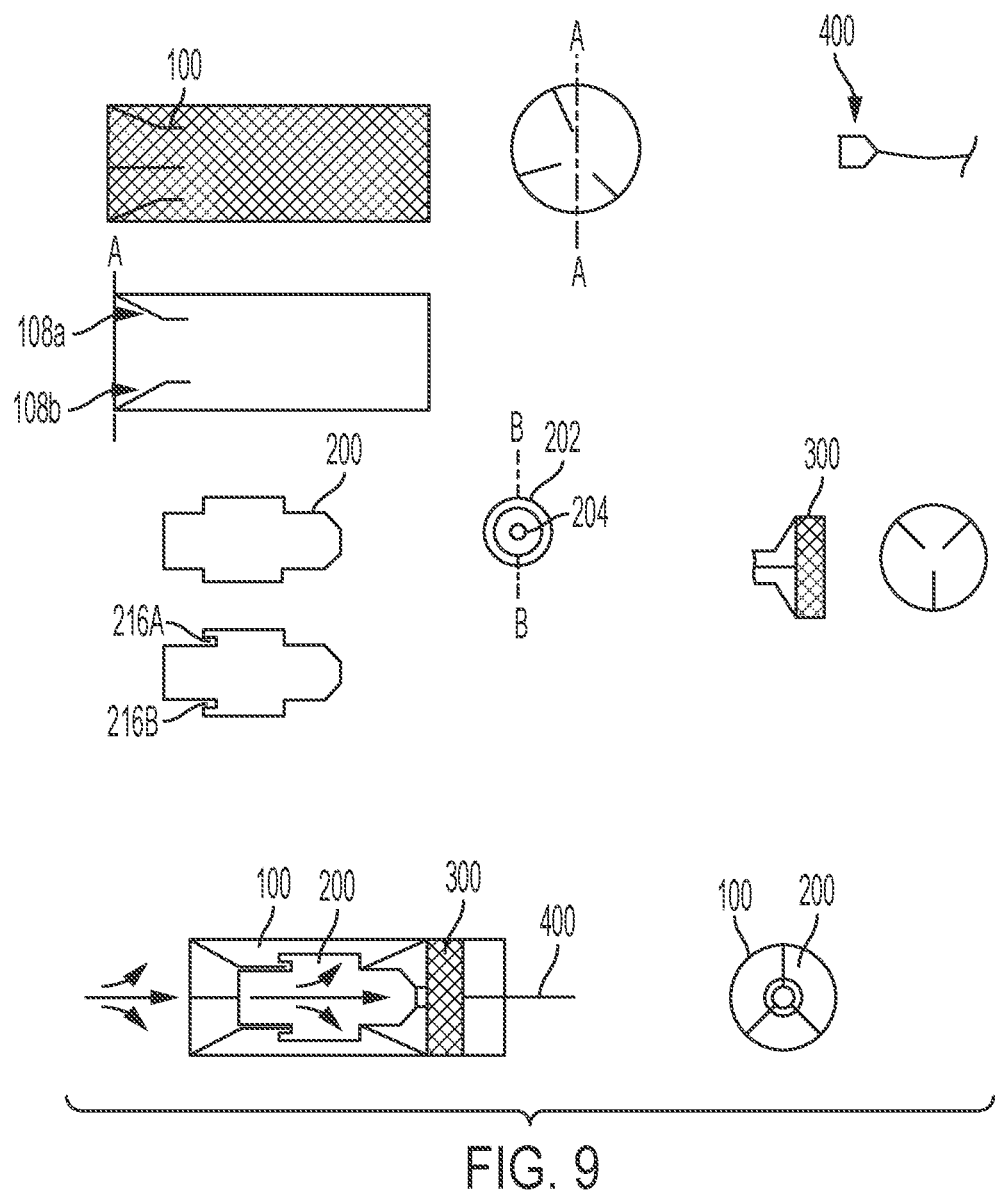
FIG. 9 is an illustration of various additional configurations for the branch member, the pump, and the retention element, according to some embodiments.

FIG. 9 shown a variety of additional configurations for the various components (e.g., the branch member 100, the pump 200, the retention element 300, and the driveline 400) of the systems disclosed herein. For instance, in some examples, the branch member 100 may include one or more support components (e.g., components "a" and "b") that project radially inwardly and are configured to interface with and support the pump 200 within the branch member 100, as shown. In some examples, the pump 200 may include one or more features that are complementary of the support components "a" and "b" of the branch member 100, and that engage therewith to couple the pump 200 to the branch member 100, such that the pump 200 is suspended within an interior of the branch member 100 (e.g., within a lumen defined by an interior of the branch member 100). As shown, the pump 200 is coaxially aligned with the branch member 100, wherein an exterior of the pump 200 is offset from an interior of the branch member 100 such that an annular void is defined between the interior of the branch member 100 and the pump 200. In various examples, blood is operable to flow through such an annular void (e.g., in conjunction with, or as an alternative to blood flow through the pump 200).

FIG. 10 is an illustration of an example branch member 100 with flanges 520a, 520b, according to some embodiments. The branch member 100 creates a fluidic connection between spaces or tissue structures such as the aorta and an atrium or ventricle as discussed in detail above. As shown, the branch member 100 includes flanges 520a, 520b. The flanges 520a, 520b may be arranged to seal the branch member 100 within tissue structures or within a main body 208 of an implantable medical device as discussed above. In instances where the branch member 100 includes two flanges 520a, 520b as shown, the main body 208 includes a fenestration (either created after implantable or prior to implantation).

The branch member 100 includes a lumen 46 that extends longitudinally from a first end of the branch member 100 to a second end of the device 40. The lumen 46 acts as a connection (e.g., a shunt passageway) between the main body 208, implanted in the aorta, and the internal intestinal space of the heart (e.g., atrium or ventricle), such that the main body 208 is in fluid communication with the atrium or ventricle via the anastomosis device branch member 100. The flange 520b may be configured to contact a tissue wall 522 as described in detail above. A wall 44 of the lumen 46 may be sized to interference fit with a pump 200.

Figure 11:
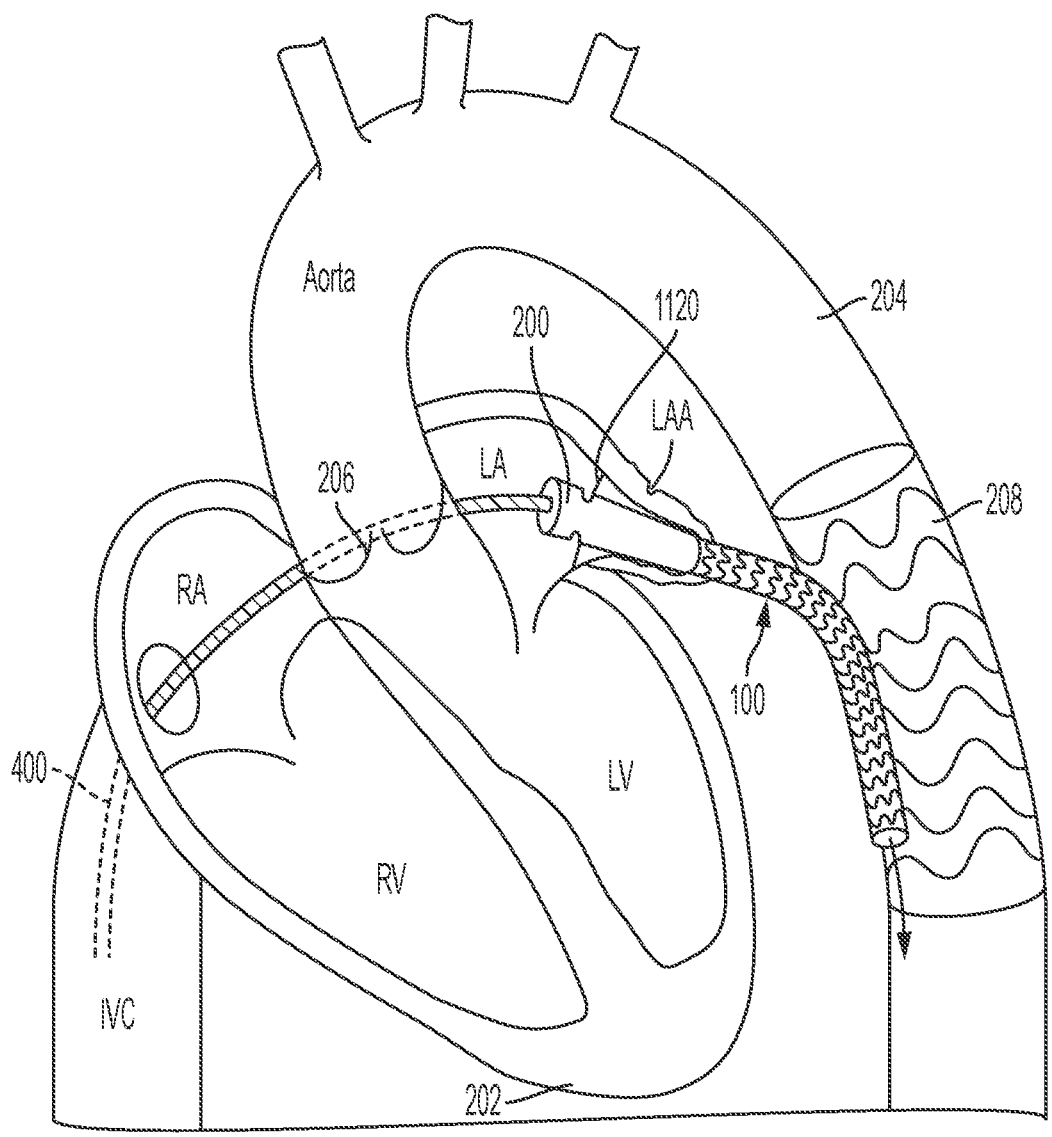
FIG. 11 is an illustration of another implantable medical device for cardiac assistance, according to some embodiments.

FIG. 11 is an illustration of another implantable medical device for cardiac assistance, according to some embodiments. The implantable medical device is shown implanted in a patient's aorta 204, and more particularly within the descending aorta 204, leading from a patient's heart 202. The patient's heart 202 is represented as a simplified diagram and includes the aortic valve 206, the right atrium (RA), left atrium (LA), right ventricle (RV), and left ventricle (LV).

In certain instances, the implantable medical device includes a main body 208 configured to deploy within the aorta 204. The main body 208 includes a lumen maintaining fluid flow through the aorta 204. In addition, the main body 208 also includes a portal coupled to the main body 208 providing access to the lumen of the main body 208. The implantable medical device may also include a branch member 100 configured to deploy within the fenestration or portal (as described, respectively, above with reference to FIGS. 2 and 6) to fluidly connect with the lumen of the main body 208. Though shown coupled to the branch member 100, in certain instances, the pump 200 may be integrated into, or otherwise coupled with the main body 208.

As referenced above, the branch member 100 may include a pump 200 configured to convey blood through the branch member 100 and into the lumen of the main body 208. The branch member 100 and pump 200 may include the structural and functional components described above with reference to system 1000. In addition and as noted above, the pump 200 is configured to increase blood flow into the aorta 204 for cardiac assistance.

As shown in FIG. 11, the pump 200 and/or branch member 100 may be arranged within a left atrial appendage (LAA) of the heart 202. The branch member 100 may exit the LAA to couple to the main body 208 arranged within the descending aorta 204. The main body 208 may be arranged within other portions of the aorta 204. In certain instances, the pump 200 and branch member 100 include a sealing element 316 or flange (e.g., as shown in FIG. 3B) to secure and position the pump 200 and branch member 100 within the LAA. In other instances, a stent structure 1120 may be coupled to the branch member 100 and/or pump 200.

In certain instances and as shown, the stent structure 1120 may contact interior walls of the LAA. The stent structure 1120, as shown in further detail in FIG. 12, may stabilize the pump 200 and/or branch member 100 within the LAA. The stent structure 1120 may be configured to conform to the shape of the LAA (e.g., including an acorn or tapered shape). In addition, the stent structure 1120 may be at least partially covered by a membrane to seal off the LAA about the pump 200 and/or branch member 100. The stent structure 1120 may include a central eyelet through which the pump 200 and/or branch member 100 are arranged. Further, the stent structure 1120, which may include the membrane, lessens turbulent blood flow across the LAA to minimize the opportunity for thrombus formation. For further discussion and detail regarding some suitable designs for the stent structure 1120, reference may be made to U.S. Patent Publication No. 2016/0331382 to Center et al, U.S. Pat. No. 9,554,806 to Larsen et al, and U.S. Patent Publication No. 2015/0005810 to Center et al, which discuss left atrial appendage medical devices.

In certain instances, the pump 200 may be coupled to a driveline 400 that is coupled to a controller configured to control the operation of the pump 200. As shown in FIG. 1, the driveline 400 may be routed through the heart 202 septum to the right atrium and through the vena cava.

In certain instances, the branch member 100 may include a portion that is arranged directly within the aorta 204 without the main body 208. In certain instances, the branch member 100 includes a first end portion configured to deploy within the left atrial appendage of a heart and a second end portion configured to deploy within the aorta 204. The branch member 100, as discussed in detail above, is configured to interface with the pump 200 to pass blood flow through a lumen of the branch member 100 from the left atrial appendage into the aorta 204. The branch member 100 may include a flange configured to engage a tissue wall of the aorta (e.g., as shown in FIG. 5 and FIG. 10). The flange may be configured to engage the tissue wall in a fluid tight fluid communication between the branch member 100 and the tissue wall of the aorta 204.

In certain instances, the branch member 100 (or pump 200) may be anastomosed to the aorta 204 (e.g., using flanges). The pump 200 may be configured to intake blood from the left atrial appendage and discharge the blood into the aorta 204. When the branch member 100 is directly coupled to the aorta 204, the outflow of the pump 200 is directly to the aorta 204 through the branch member 100.

Figure 12:
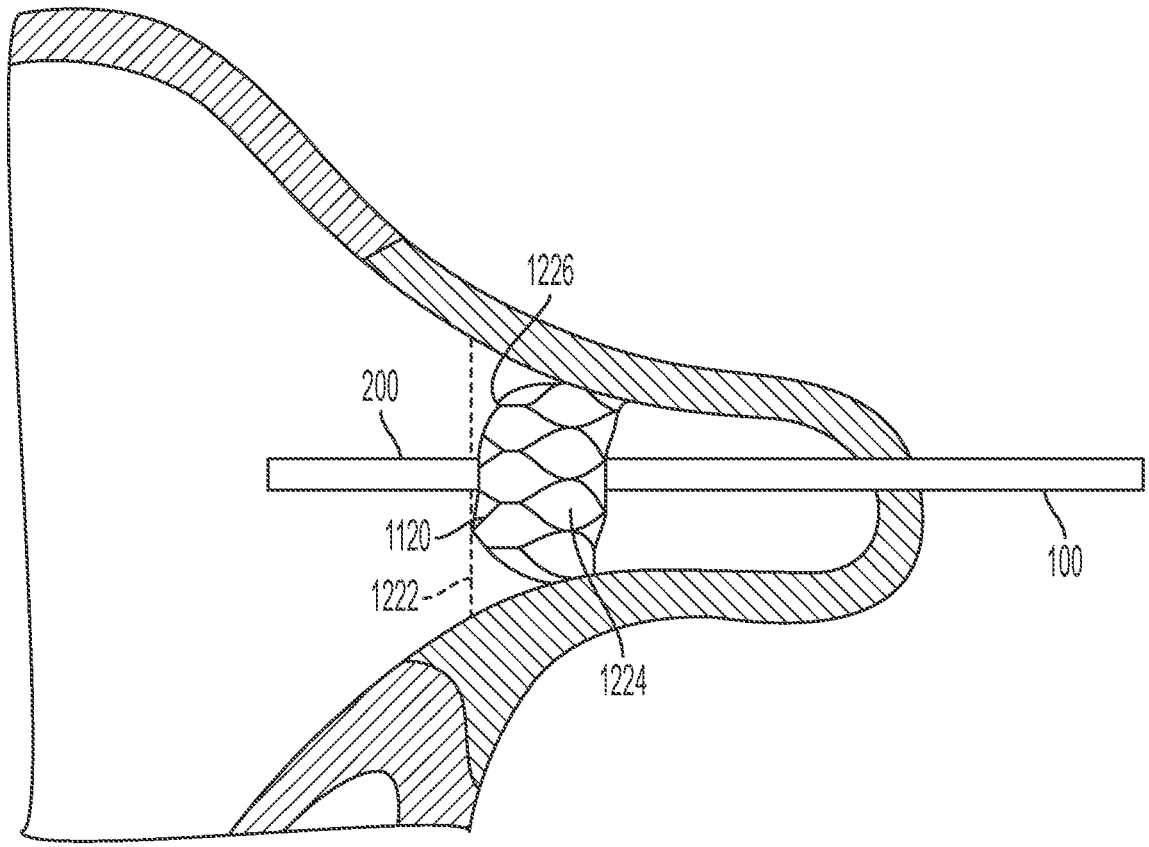
FIG. 12 is an illustration of another implantable medical device for cardiac assistance arranged within a left atrial appendage and including a stent structure, according to some embodiments.

FIG. 12 is an illustration of another implantable medical device for cardiac assistance arranged within a left atrial appendage and including a stent structure 1120, according to some embodiments. As shown, the pump 200 and branch member 100 is arranged through the stent structure 1120. The stent structure 1120 may include an occlusive face that is arranged near an ostium 1222 of the left atrial appendage. In addition and as shown, the stent structure 1120 includes frame components 1226 and a membrane 1224 covering the frame components.

Figure 13:
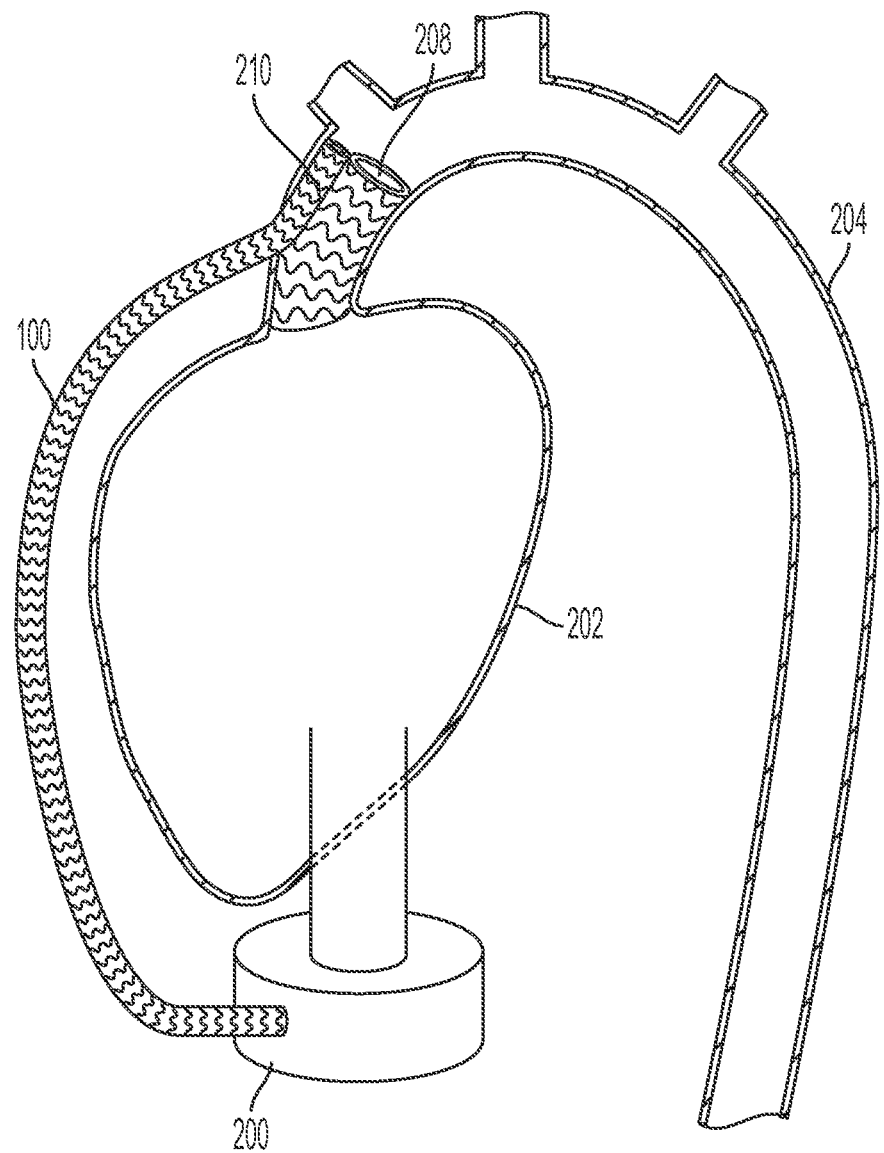
FIG. 13 is an illustration of an example implantable medical device for cardiac assistance, according to some embodiments.

FIG. 13 is an illustration of an example implantable medical device for cardiac assistance, according to some embodiments. The system 1000 may be used as an implantable medical device for cardiac assistance as shown in FIG. 13. As shown in FIG. 13, a main body 208 portion of an implantable medical device is arranged within a patient's aorta 204 leading from a patient's heart 202. The patient's heart 202.

The main body 208 includes a lumen maintaining fluid flow through the aorta 204. In addition, the main body 208 also includes an access site 210 in a sidewall of the main body 208 providing access to the lumen of the main body 208. The access site 210 may be a fenestration created before or after implantation of the main body 208. In addition, the main body 208 may include radiopaque markers arranged near adjacent the access site 210 to facilitate deployment. Further, the access site 210 may be deployed as facing away from the brachiocephalic, subclavian, and carotid arteries.

The main body 208 may include a curvature or conform to a curvature of the aorta with the access site 210 being arranged opposite the curvature and thus be arranged as facing away from the brachiocephalic, subclavian, and carotid arteries.

The implantable medical device may also include a branch member 100 configured to deploy within the access site 210 to fluidly connect with the lumen of the main body 208. As noted above, to facilitate coupling of the branch member 100 and the main body 208, the access site 210 of the main body 208 fluidly connects with the lumen of the main body 208. The access site 210 in the main body 208 may include a fenestration or a portal.

As shown in FIG. 13, the branch member 100 is arranged external to the heart 202. In certain instances, the branch member 100 is arranged about a patient's heart 202. The implantable medical device may also include a pump 200 arranged within a chamber of the heart 202 that is configured to convey blood through the branch member 100 and into the lumen of the main body 208. In certain instances, the pump 200 is configured to be disposed within a left ventricle of the patient's heart 202 and convey blood through the branch member 100 and into the lumen of the main body 208.

Implanting the branch member 100 to connect the pump 200 to the main body 208 in the aorta may function as a cardiac assist device with the pump 200 forcing blood from one or more chambers of the heart into the aorta 204. The branch member 100, main body 208, and pump 200 may be used to assist heart function for patients' having weakened hearts or heart failure. In addition and as noted above, the pump 200 may be configured to increase blood flow into the aorta 204 for cardiac assistance.

To deliver the branch member 100 and connect the aorta 204 and the pump 200, a puncturing device (e.g., arranged through the access site 210) creates a small access site in a tissue wall of the aorta 204. The branch member 100 may be arranged within the access site 210 after puncturing the aorta 204 (which may then be sealed (e.g., the main body 208 seals within and external to the aorta 204 by having an overlap between the branch member 100 and the access site 210). The branch member 100, for example, may include stent-and graft components (as noted above with reference to FIG. 1) that allow for flexibility and relative motion between the aorta 204 and the pump 200.

In addition, the branch member 100 and pump 200 combination provides direct increase of blood flow for cardiac assistance. The branch member 100 and pump 200 may be configured to deliver the blood flow through the branch member 100 and into the lumen of the main body 208 parallel to native blood flow through the aorta 204. The branch member 100, the main body 208, and the pump 200 may be collapsed to a delivery configuration of transcatheter delivery. Having the main body 208 arranged in the aorta 204 mitigates the risk of aortic dissection, protects the aortic wall from an increased fluid flow from the pump 200, and may reduce risk of device deployment Arranging the main body 208 and the branch member 100 and pump 200 in this manner facilitates connection of a pump 200 to the aorta 204 without an additional open heart procedure. The main body 208 and the branch member 100 and pump 200 may be sutureless, percutaneous, and anastomotic. The main body 208 and the branch member 100 and pump 200 may also provide in-line (or parallel) flow that can reduce shear and turbulence which could damage the blood or consume blood proteins, and potentially reduces backpressure on the heart. The main body 208 and the branch member 100 and pump 200 may also protects the aorta locally from shear-induced damage (e.g., dissection, intimal hyperplasia) and/or decouples the motion of the heart from the motion of the aorta 204, allowing native motion while minimizing the risk of erosion or pull-out. In certain instances, the branch member 100 may be arranged directly within the aorta 204 without the main body 208.

Figure 14:
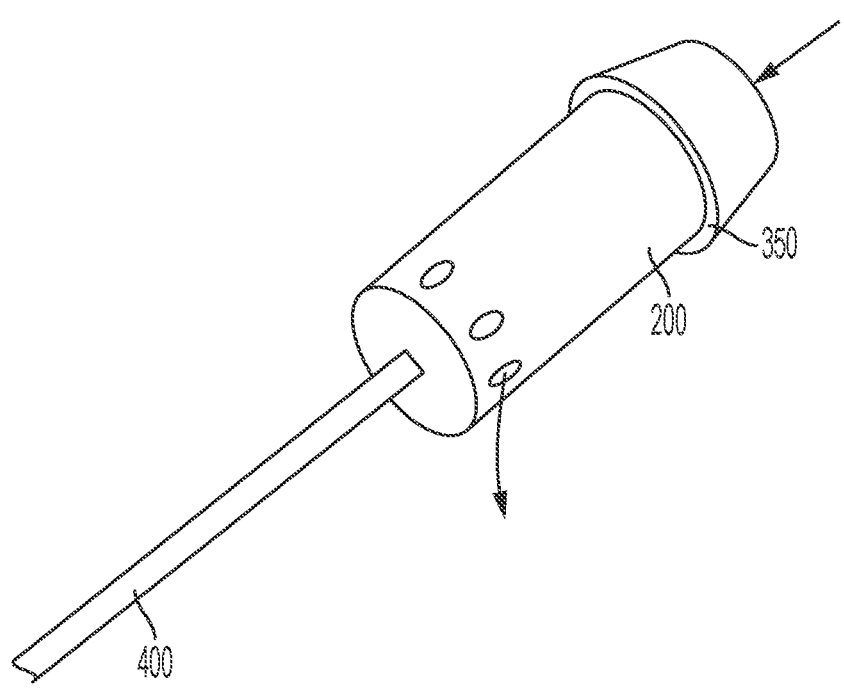
FIG. 14 is an illustration of an example implantable medical device for cardiac assistance for implantation into a pulmonary vein, according to some embodiments.

FIG. 14 is an illustration of an example implantable medical device for cardiac assistance for implantation into a pulmonary vein, according to some embodiments. The implantable medical device may be a pump 200, or in other instances, the implantable medical device may be a pump 200 that deploys within a main body that may include a stent, graft, or stent-graft combination for implantation into a vessel of a patient. In certain instances, the implantable medical device is configured to deploy within a pulmonary vein 350 and the implantable medical device includes a lumen maintaining fluid flow through the pulmonary vein 350. In certain instances, the pump 200 may be arranged within the vena cava (inferior or superior) to facilitate right ventricular assistance. The pump 200 may be arranged within a branch member 100 in certain instances and arranged within the vena cava. In other instances, the pump 200 (with or without the branch member 100) may be arranged within the descending or thoracic aorta, or peripheral vessels to facilitate blood flow. In addition, the pump 200 (with or without the branch member 100) may increase flow of other non-blood bodily fluids when placed in other areas of the body (e.g., urinary, biliary).

The implantable medical device may also include a pump 200 arranged within the main body of the implantable medical device that is configured to convey blood through the lumen of the main body. In certain instances, the pump 200 is configured to intake blood flow into the left atrium 352. In addition, the pump 200 may be configured to increase flow out of the pulmonary vein 350 to increase cardiac output.

In certain instances, the pump 200 includes a driveline 400 configured to power the pump 200. The driveline 400 may be coupled to the pump 200 and arranged out of the pulmonary vein 350 into the left atrium 352 and across a septum to exit a right side of the heart. In certain instances, the driveline 400 exits a patient via an iliac vein. The pump 200 may facilitate direct filing of the ventricles when the pump 200 is implanted in the pulmonary vein 350. The pump 200 being implanted into the pulmonary vein 350 may facilitate increased pulmonary circulation, decrease risk of chronic obstructive pulmonary disease (COPD), increase cardiac output, and implant a cardiac assistance device using venous access, which can reduce access site complications as compared to arterial access.

In certain instances, the pump 200 may be used to facilitate flow within another vessel. The pump 200 may be implanted for vessel-vessel communication (e.g., percutaneous fistula creation). In addition, the pump 200 may include or be coupled to a drug delivery reservoir with the pump 200 pumping blood and a therapeutic drug within a patient. In other instances, the pump 200 may include a sensor used to sample blood within a patient. In addition, the sensor may be incorporated with the pump to measure blood flow and indicate the flow to a physician for monitoring.

Figure 15:
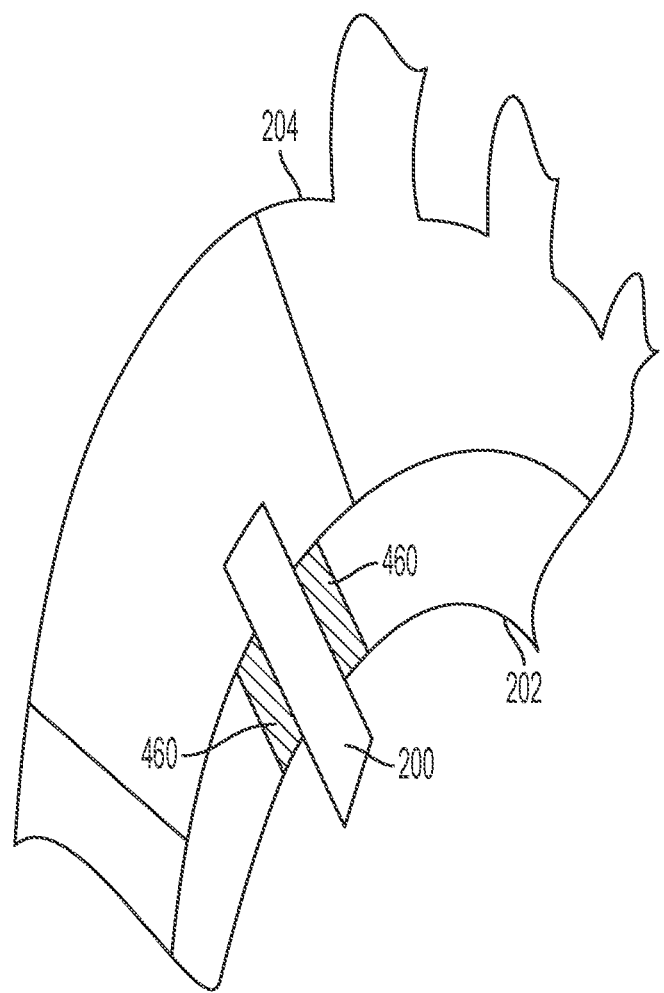
FIG. 15 is an illustration of an example implantable medical device for cardiac assistance, according to some embodiments.

FIG. 15 is an illustration of an example implantable medical device for cardiac assistance, according to some embodiments. As shown in FIG. 15, a pump 200 is arranged between a patient's aorta 204 and a patient's heart 202. The pump 200, in certain instances, is arranged in the left atrium, right atrium or left ventricle. The pump 200 is configured to force blood flow from the heart chamber into the aorta 204.

To seal the pump 200 in the heart 202 and the aorta 204, a conduit of native tissue 460 about the pump and between the aorta and the heart chamber. In certain instances, the conduit of native tissue 460 may be formed by creating or tissue ingrowth to form a tissue layer between the aorta 204 and the heart 202. The pump 200 may include a material arranged about an outer surface of the pump 200 that configured to facilitate tissue ingrowth. In certain instances, the material includes at least one of Dacron and ePTFE The material may be a graft or covering component that can have a microporous structure that provides a tissue ingrowth scaffold. In certain instances, the covering component may include a fluoropolymer, such as an expanded polytetrafluoroethylene (ePTFE) polymer. In some examples, the covering component can be a membranous covering. In some examples the covering component can be a film. The covering component may be modified with covalently attached heparin or impregnated with one or more drug substances that are released in situ to promote wound healing. In some instances, the drug may be a corticosteroid, a human growth factor, an anti-mitotic agent, an antithrombotic agent, or dexamethasone sodium phosphate.

After the conduit of native tissue 460 is formed, the pump 200 may be removed. In certain instances, the conduit of native tissue 460 may be relined with another material (e.g., a membrane or graft material) after the conduit of native tissue 460 is formed.

Figure 16A:
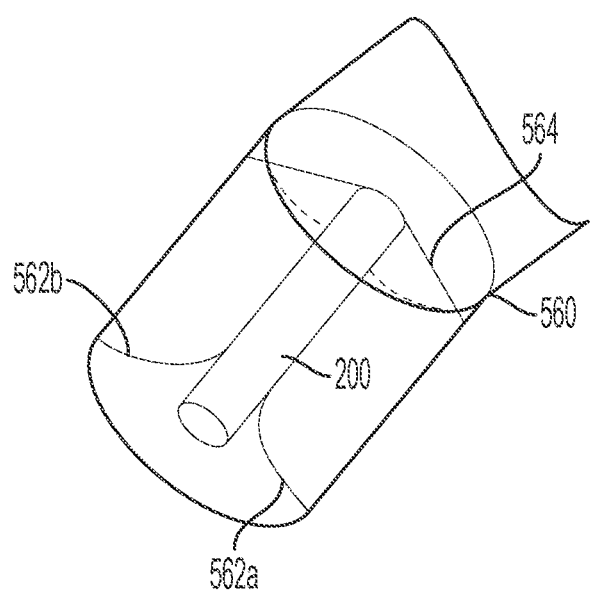
FIG. 16A is a top view of an example implantable medical device for cardiac assistance for implantation as a heart valve, according to some embodiments.
Figure 16B:
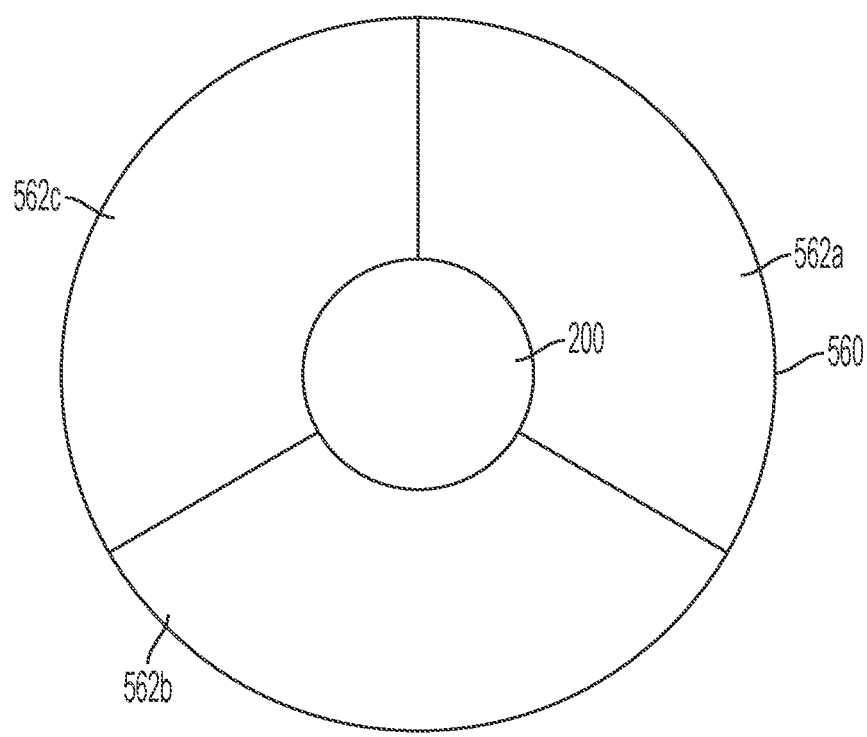
FIG. 16B is an illustration of the example implantable medical device shown in FIG. 16A arranged as a heart valve, according to some embodiments.

FIG. 16A is a top view of an example implantable medical device for cardiac assistance for implantation as a heart valve, according to some embodiments. FIG. 16B is an illustration of the example implantable medical device shown in FIG. 16A arranged as a heart valve, according to some embodiments. The implantable medical device is a heart valve device that includes a support frame 560. A plurality of leaflets 562a-c are coupled to the support frame 560. The plurality of leaflets 562a-c are configured to open to allow forward flow therethrough and to occlude the support frame 560 to prevent retrograde flow. A pump 200 may also be arranged with the support frame 560. The pump 200 may be configured to force blood through the support frame 560.

In certain instances and as shown in FIG. 16B, the plurality of leaflets 562a-c are configured to coapt about the pump 200 arranged within the support frame 560. The pump 200 may be arranged centrally within the support frame 560, with the leaflets 562a-c closing onto the pump 200. The prosthetic valve (the support frame 560 and the leaflets 562a-c) and the pump 200 may configured to transcatheter delivery. In certain instances, the prosthetic valve is configured to replace an aortic valve of a patient and in other instances, the prosthetic valve is configured to replace a mitral valve of a patient.

In certain instances, a filter 564 may be arranged on an outflow end of the support frame 560. More specifically, the filter 564 may be arranged at the outflow end of the pump 200. The filter 564 may facilitate protection against emboli passing through the support frame 560.

A method of delivering the support frame 560 and pump 200 via a catheter can comprise providing a delivery catheter having an expandable support frame 560 in a collapsed state constrained over or within the delivery catheter at a distal end of the delivery catheter; passing the delivery catheter through the introducer sheath and into valve annulus; positioning the distal end of the delivery catheter so that the support frame 560 is properly positioned and oriented within the valve annulus; and expanding the support frame 560 at the valve annulus into contact therewith.

Figure 17:
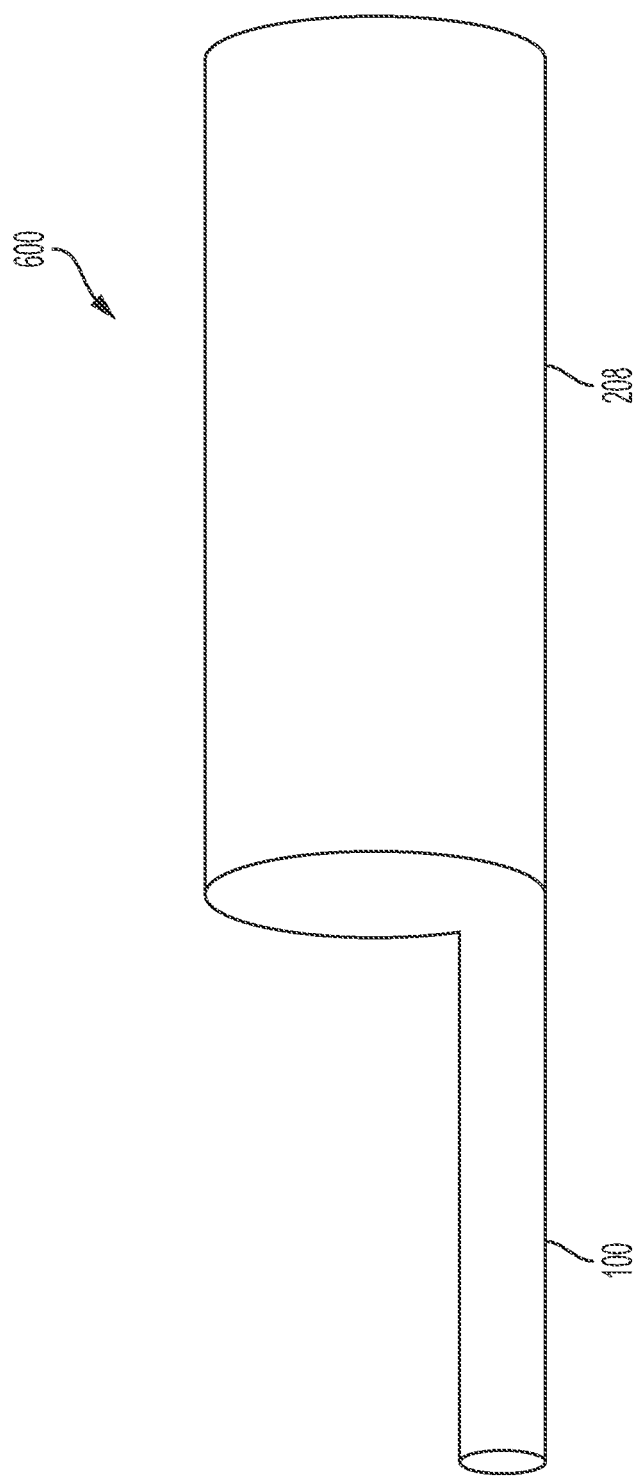
FIG. 17 is an illustration of an example implantable medical device for cardiac assistance, according to some embodiments.

FIG. 17 is an illustration of an example implantable medical device 600 for cardiac assistance, according to some embodiments. System 1000 may form a portion of the implantable medical device 600 for cardiac assistance shown in FIG. 17. For example, the implantable medical device 600 includes a main body 208 portion that is configured to be deployed within a patient's aorta leading from a patient's heart. The implantable medical device 600 may also include a branch member 100 extending from the main body 208 and configured to deploy within a chamber of the heart to fluidly connect the aorta and the chamber of the heart. In certain instances, the branch member 100 may be integral with the main body 208. The branch member 100 may extend from an end portion of the main body 208 (as shown in FIG. 17) or the branch member 100 may extend from circumferentially from the main body 208.

The branch member 100 being integral with or forming a portion of the main body 208 may facilitate deployment of the main body 208 and the branch member 100 from same deployment location, direction, or using the same catheter device. In certain instances, the main body 208 may be arranged within the aorta via the femoral artery and into the aorta. After deploying the main body 208, punctures may be made in the aorta and a chamber of the heart (atrium or ventricle) via the same femoral access. In certain instances, a guidewire used to deploy the main body 208 may be used to puncture tissue in the aorta and the chamber of the heart. Immediately after puncturing the aorta and the chamber of the heart, the branch member 100 may cross the aorta and the chamber of the heart. In certain instances, puncture and delivery of the branch member 100 may occur in the same action (e.g., using the same guidewire). Thus, leakage may be minimized by deploying the branch member 100 in an immediately sequence. In addition, the deployment and puncturing may occur using a singular delivery handle/system.

The implantable medical device 600 may also include a pump 200 (not shown). As discussed in detail above, the pump 200 may be arranged within the branch member 100 and configured to force blood flow from the chamber of the heart through the branch member 100 and into the lumen of the main body 208. To deploy the pump 200, the pump 200 may be arranged through the inferior vena cava (IVC), across the septum of the heart and deployed with the branch member 100.

The main body 208 and the branch member 100 may include stent, graft, or stent and graft components. In addition, the branch member 100 may be configured to telescope inwardly and outwardly relative to the main body 208. In certain instances, the branch member 100 may collapse and extend to alter a length of the branch member 100.

Figure 18:
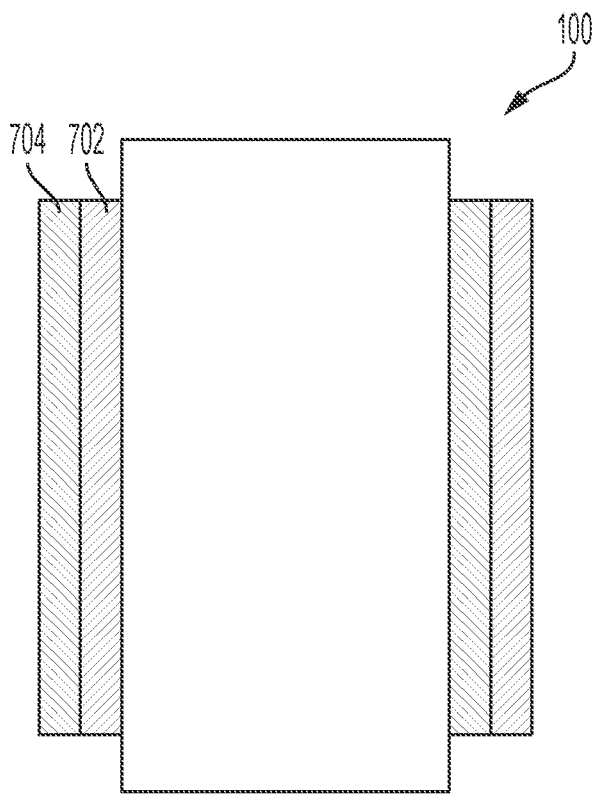
FIG. 18 is an illustration of an example branch member, according to some embodiments.

FIG. 18 is an illustration of an example branch member 100, according to some embodiments. As noted above, the branch member 100 may be configured to interface with a pump (not shown) to pass blood flow through the branch member 100 into the main body. In other instances, the branch member 100 may a support frame used in a prosthetic valve (e.g., as shown in FIGS. 16A-B). The branch member 100 (or support frame) may be delivered to a target location and removably couple to a pump after the branch member 100 has been delivered and deployed within the patient (e.g., a branch member of an implantable medical device).

In certain instances, the branch member 100 (or support frame) may be configured to anchor the pump within the branch member. As shown in FIG. 18, for example, the branch member 100 (or support frame) may include an attachment mechanism 702 that is configured to anchor the pump with the branch member 100 (or support frame). In certain instances, each of the branch member 100 (or support frame) and the pump may include complementary attachment mechanisms 702, 704 to anchor the pump within the branch member 100. In addition and alternatively to the attachment mechanism 702 or complementary attachment mechanisms 702, 704, the branch member 100 (or support frame) may be configured to frictionally engage with the pump to anchor the pump within the branch member 100.

Figure 19A:
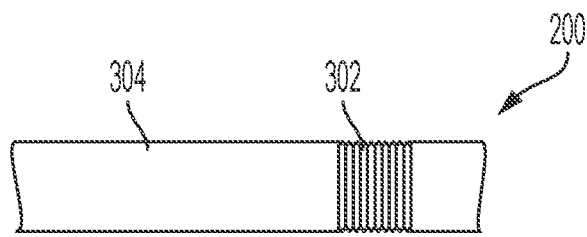
FIG. 19A is an illustration of a pump and a hinge structure in a first configuration, according to some embodiments.
Figure 19B:
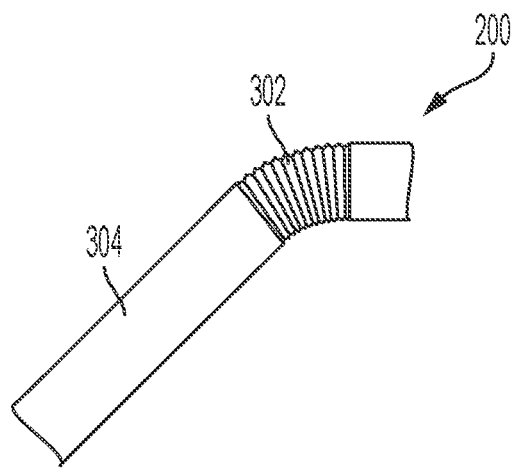
FIG. 19B is an illustration of the pump and hinge structure, as shown in FIG. 19A, in a second configuration, according to some embodiments.

FIG. 19A is an illustration of a pump 200 and a hinge structure 302 in a first configuration, according to some embodiments. The hinge structure 302 may be the anchor element for the pump 200. In certain instances, the hinge structure 302 is configured to articulate a portion of the pump 200 and maintain the pump 200 in an angled configuration as shown in FIG. 19B. The hinge structure 302 may maintain the pump 200 at an angle after a force is applied to alter the configuration of the pump 200.

In certain instances, the pump 200 includes a tubular portion 304 and the hinge structure 302 is arranged circumferentially within or about the tubular portion 304. In addition, the pump 200 may have multiple hinge structures 302 arranged at different positions along a length of the tubular portion 304. Multiple hinge structures 302 may facilitate bending of the tubular portion 304 at different angles and/or initiate bending at different portions along a length of the tubular portion 304. Bending at the hinge structure 302 creates fixation between the pump 200 and the branch member 100.

The hinge structure 302 may include a plurality of discrete rings configured to maintain the tubular portion 304 in the angled configuration in response to an applied force. In certain instances, the discrete rings of the hinge structure 302 may be metal stent-like structures. In addition, the hinge structure 302 may also be formed by a corrugated portion of the tubular portion 304. The tubular portion 304, along with a motor and impeller as described above with reference to FIG. 1, may include a stent, a stent-graft, or a graft. In certain instances, the corrugated portion of the tubular portion 304 may be formed of a graft material. In addition and as noted above with reference to FIG. 1, the pump 200 may include a driveline configured to couple to a controller that drives the pump 200.

The pump 200 may be delivered into branch member 100 by a catheter. The catheter may be deflected to angle the hinge structure 302. In instances where the pump 200 is to be removed, a catheter may be routed to the branch member 100, and the hinge structure 302 may be un-articulated. The hinge structure 302 may engage with a branch member 100 arranged in a portal or a fenestration of a main body graft. In addition, the hinge structure 302 may be include a shape memory material (e.g., Nitinol) such that the hinge structure 302 is arranged in a substantially linear configuration (e.g., as shown in FIG. 19A) during delivery but shape set into an elbow or angled configuration (as shown in FIG. 19B). In these instances, the hinge structure 302 will deploy to the angled configuration after delivery and engage the branch member 100.

Figure 20:
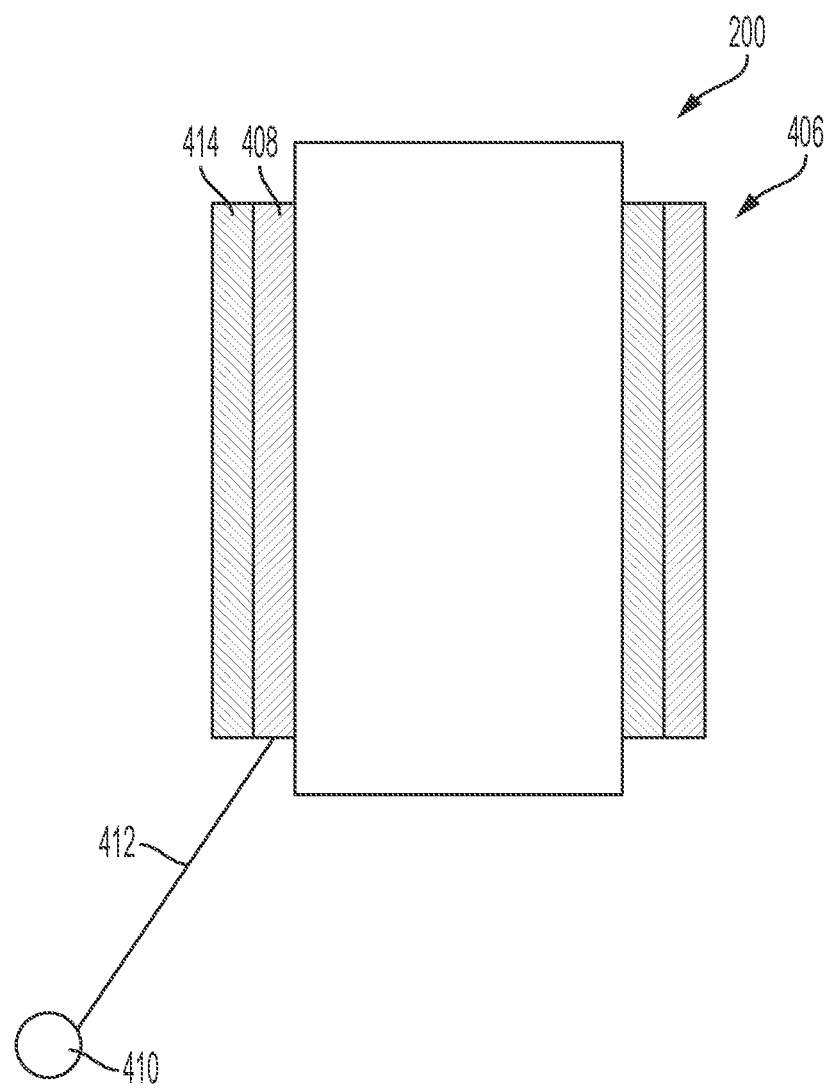
FIG. 20 is an illustration of an example pump and anchor element, according to some embodiments.

FIG. 20 is an illustration of an example pump 200 and anchor element 406, according to some embodiments. As shown in FIG. 4, the anchor element 406 is arranged on an external surface of the pump 200. The anchor element 406 may be configured to expand and engage an interior surface of a branch member.

In certain instances, the anchor element 406 is an expandable balloon 408 configured to expand and engage an interior surface of the branch member. The expandable balloon 408 may be coupled to an inflation/deflation pump 410 by way of a conduit 412. The inflation/deflation pump 410 may be arranged internal or external to the patient and the conduit 412 may be routed similar to the driveline. In certain instances, the expandable balloon 408 may be arranged circumferentially about the pump 200.

In certain instances, the anchor element 406 is or includes spring 414 arranged on the external surface of the pump 200. The anchor element 406 may also include the expandable balloon 408, which is configured to collapse the spring 414 in response to inflation. In certain instances, the expandable balloon 408 may be deflated to collapse the spring and close a gap between the pump 200 and the branch member.

In either instance, the expandable balloon 408 may be inflated and deflated to reposition the pump 200. In addition, the expandable balloon 408 creates an interference fit between the pump 200 and the branch member. The expandable balloon 408 may be filled with liquid (e.g., saline, contrast medium) or air. in addition, the expandable balloon 408 may be backfilled with curing fluid that solidifies if the pump 200 is permanently implanted within the branch member 100. the curing fluid may also be dissolvable such that the pump 200 is not permanently implanted within the branch member 100.

Figure 21:
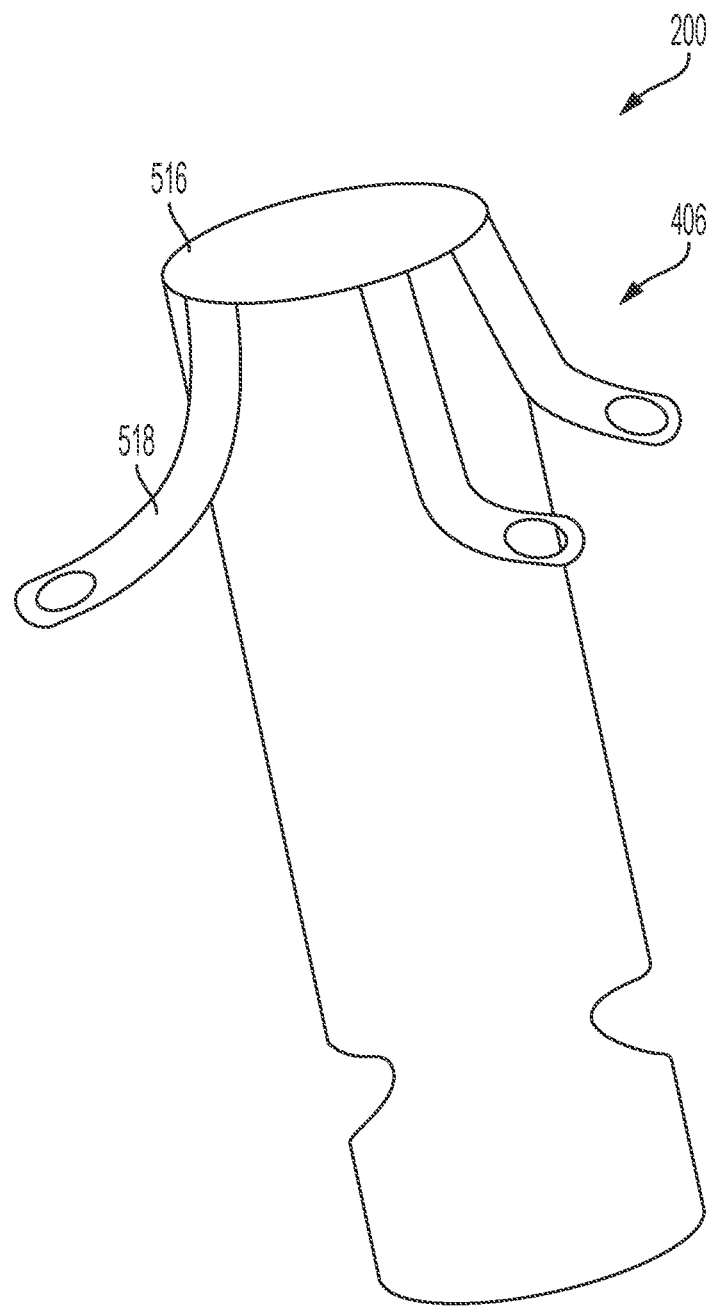
FIG. 21 is an illustration of another example pump and anchor element, according to some embodiments.

FIG. 21 is an illustration of another example pump 200 and anchor element 406, according to some embodiments. As shown in FIG. 21, the anchor element 406 is arranged at an end portion 516 of the pump 200. In addition, the anchor element 406 includes a plurality of flanges 518 extending radially from the end portion 516 of the pump 200.

The flanges 518 may include a self-expanding material (e.g., Nitinol) that extend radially from the end portion 516 of the pump 200. The pump 200 may be arranged within a delivery sheath and the flanges 518 may extend after the pump 200 is arranged out of the delivery sheath. In certain instances, the pump 200 may be arranged directly between the aorta and an atrium or ventricle with the flanges 518 deploying within the aorta without a main graft. In these instances, the flanges 518 may be configured to facilitate tissue ingrowth.

Figure 22:
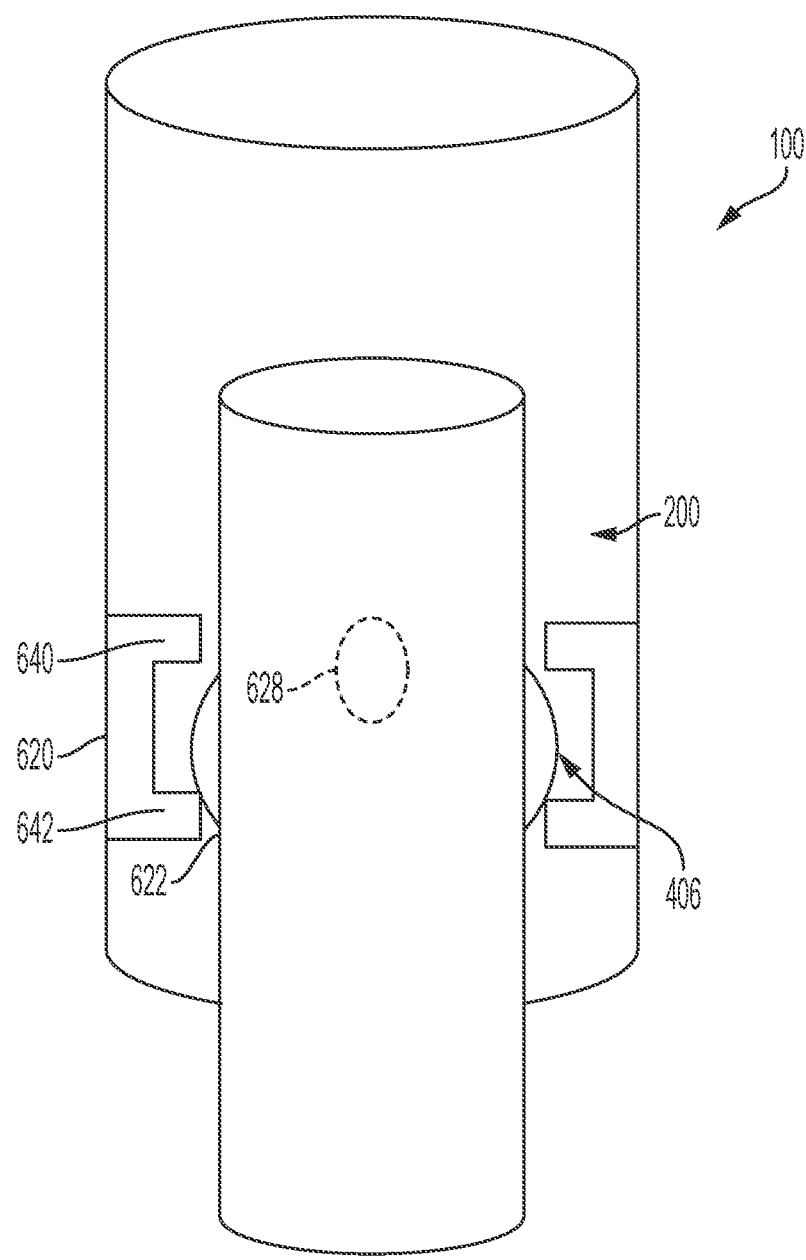
FIG. 22 is an illustration of an example branch member, pump, anchor element, and receiving structure, according to some embodiments.

FIG. 22 is an illustration of an example branch member 100, pump 200, anchor element 406, and receiving structure 620, according to some embodiments. As shown in FIG. 22, the pump 200 is arranged within and engaged with the branch member 100. The pump 200 includes the anchor element 406 along an external surface of the pump 200 and the branch member 100 includes the receiving structure 620 along an internal surface of the branch member 100. The anchor element 406 is configured to engage the receiving structure 620 to removably fix the pump within the branch member. In certain instances, the anchor element 406 is a stent 622 and the receiving structure 620 is configured to contain the stent 622 to removably fix the pump 200 within the branch member 100.

In certain instances, the stent 622 is self-expanding after the pump 200 is arranged out of a delivery sheath. In addition, the stent 622 may be elastic such that movement of the pump 200 into the branch member 100 overcomes friction of the and receiving structure 620 and nests within the receiving structure 620. The receiving structure 620 may include end portions 640, 642 that produced outwardly and create nesting area of the stent 622.

As shown, there are more than one of each of the stent 622 and the receiving structure 620. In certain instances, the stent 622 and the receiving structure 620 may be discrete elements about the outer circumference of the pump 200 and the branch member 100, respectively. There may be any number of the stent 622 and the receiving structure 620 including one, two, three, four, five, or more of each of the stent 622 and the receiving structure 620. The number of receiving structure 620 and the number of stents 622 may be unequal in number. In certain instances, there may be a greater number of receiving structures 620 to facilitate docking of the stents 622. In other instances, one or both of the stent 622 and the receiving structure 620 are discrete elements and the other of the stent 622 and the receiving structure 620 may be continuous. In certain instances, both the stent 622 and the receiving structure 620 are continuous. In addition, the stent 622 may be arranged on the internal surface of the branch member 100 and the receiving structure 620 may be arranged on the external surface of the pump 200.

The stent 622 may be spring-like and may facilitate removal of the pump 200 from the branch member 100. The pump 200 may include an engagement feature 628 that may be snared or grasped in removing the pump 200 from the branch member 100. After gripping or grasping the engagement feature 628, the pump 200 may be withdrawn and the elasticity of the stent 622 may temporarily collapse against the pump 200 and move past the receiving structure 620.

Figure 23:
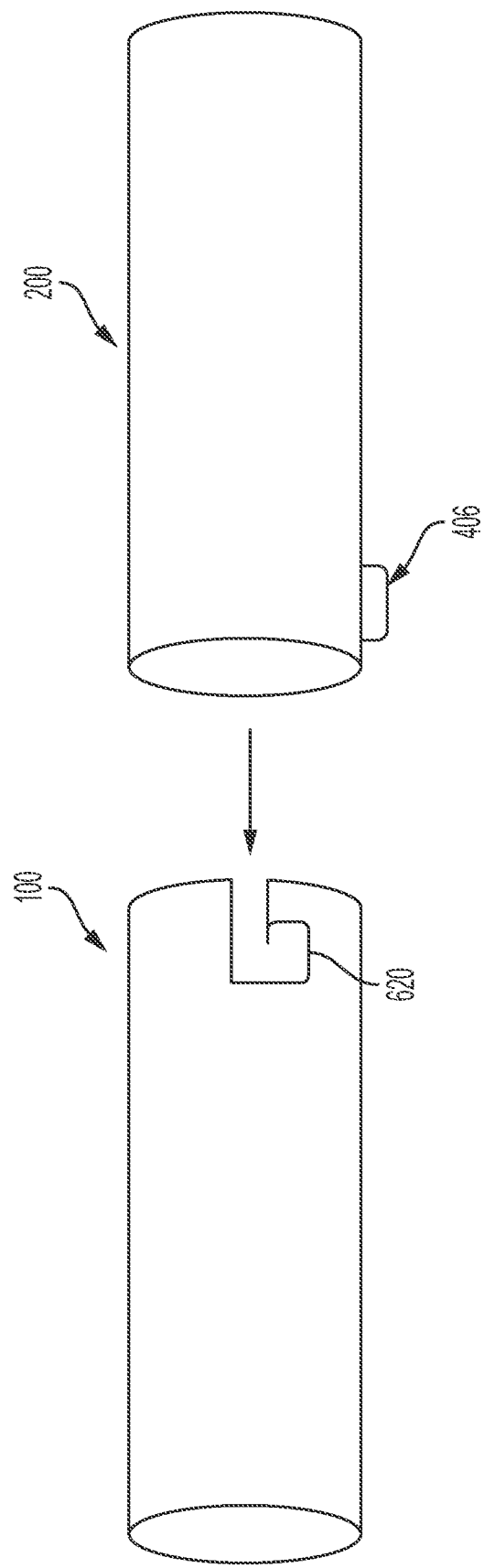
FIG. 23 is an illustration of another example branch member, pump, anchor element, and receiving structure, according to some embodiments.

FIG. 23 is an illustration of another example branch member 100, pump 200, anchor element, and receiving structure, according to some embodiments. In certain instances, the anchor element is a protrusion 406 and the receiving structure is a shaped notch 620 configured to contain the protrusion 406 may removably fix the pump 200 within the branch member 100. The protrusion 406 may be arranged with the pump 200 and the shaped notch 620 may be arranged with the branch member 100, as shown, protrusion 406 may be arranged with the branch member 100 and the shaped notch 620 may be arranged with the pump 200.

The shaped notch 620 may be a j-shaped hook that facilitates torque locking between the branch member 100 and the pump 200. The protrusion 406 may be arranged within the shaped notch 620 to releasably lock the branch member 100 and the pump 200 together.

In certain instances, the pump 200 is configured to facilitate engagement between the anchor element 406 and the notch 620. As noted above with reference to FIG. 1, the pump 200 is coupled to a controller. The controller may include options for different torques, speeds, rotations per minute (RPM), treatment schedules, or other parameters for the pump 200. When initially arranged within the branch member 100, a torque, speed, or RPMs may be selected that overcomes friction between the protrusion 406 and the shaped notch 620 to drive the protrusion 406 into locking engagement with the shaped notch 620. In certain instances, the torque, speed, or RPMs may be higher than an operating torque, speed, or RPM to overcome friction between the protrusion 406 and the shaped notch 620 to drive the protrusion 406 into locking engagement with the shaped notch 620.

Figure 24:
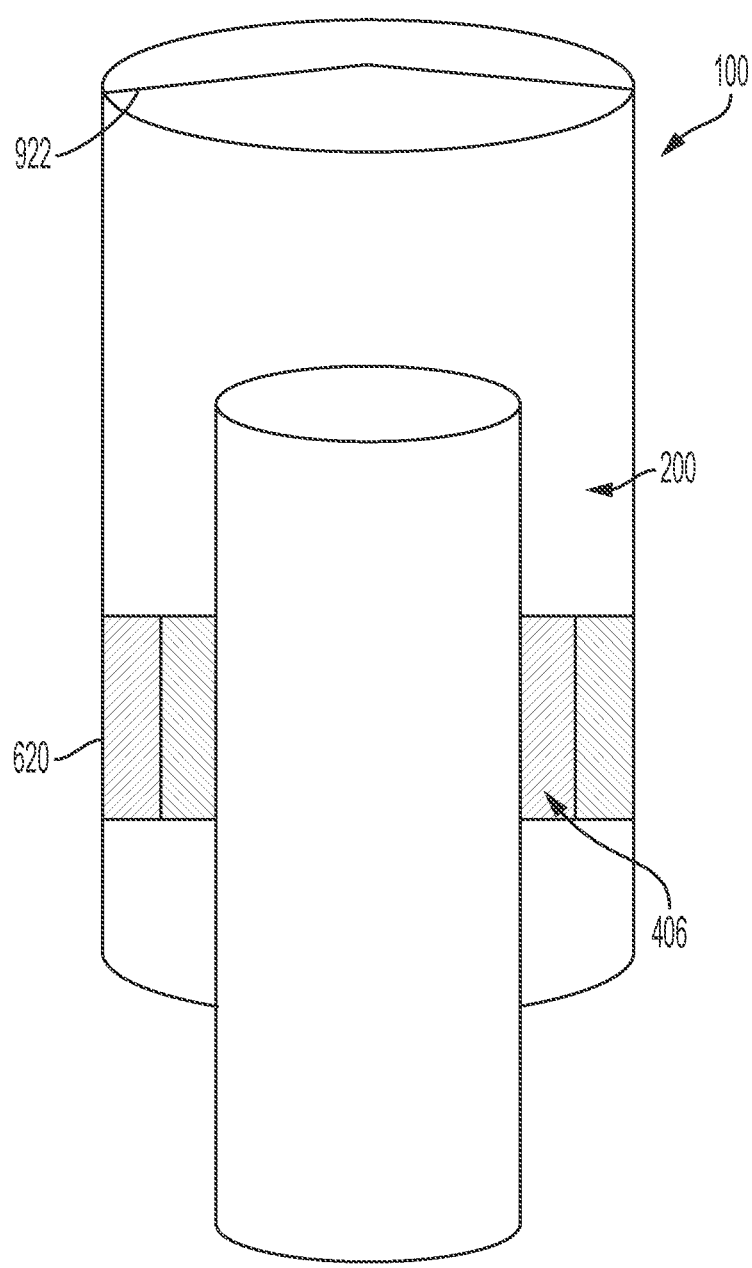
FIG. 24 is an illustration of another example branch member, pump, anchor element, and receiving structure, according to some embodiments.

FIG. 24 is an illustration of another example branch member 100, pump 200, anchor element, and receiving structure, according to some embodiments. In certain instances, the anchor element is a first threaded member 406 and the receiving structure is a second threaded member 620. The first threaded member 406 and the second threaded member 620 may be oppositely threaded. In addition, the first threaded member 406 and the second threaded member 620 are configured to engage to removably fix the pump 200 within the branch member 100. In other instances, the anchor element and the receiving structure may be magnetic instead of threaded features. In addition, the first threaded member 406 and the second threaded member 620 may be polymeric, balloon expandable, or self expanding.

In certain instances, the pump 200 is configured to facilitate engagement between the first threaded member 406 and the second threaded member 620. As noted above with reference to FIG. 1, the pump 200 is coupled to a controller. The controller may include options for different torques, speeds, or rotations per minute (RPM) for the pump 200. When initially arranged within the branch member 100, a torque, speed, or RPMs may be selected that threads of the first threaded member 406 and the second threaded member 620 are drive into locking engagement. In certain instances, the torque, speed, or RPMs may be higher than an operating torque, speed, or RPM to thread the first threaded member 406 and the second threaded member 620 together.

In certain instances, the pump 200 and the branch member 100 may be interference fit together. The anchor element 406 and the receiving structure 620 may be integral structures along a length of the branch member 100 and pump 200 to anchor the branch member 100 and pump 200 together. In addition, the anchor element 406 and the receiving structure 620 may be expandable elements to facilitate the friction or interference fit. In certain instances, the anchor element 406 and the receiving structure 620 are representative of a portion of the branch member 100 and pump 200 (e.g., sleeve, balloon, or swellable material) that expands after the pump 200 is pushed into place.

In addition and in certain instances, the branch member 100 (or pump 200) may include a valve 922 at an outflow end of the branch member 100. The valve 922 may close to prevent backflow through the pump 200 when the pump 200 is not in operation. The valve 922 may include a graft material, film, or a metal (e.g., Nitinol, stainless steel) or a combination thereof.

Figure 25:
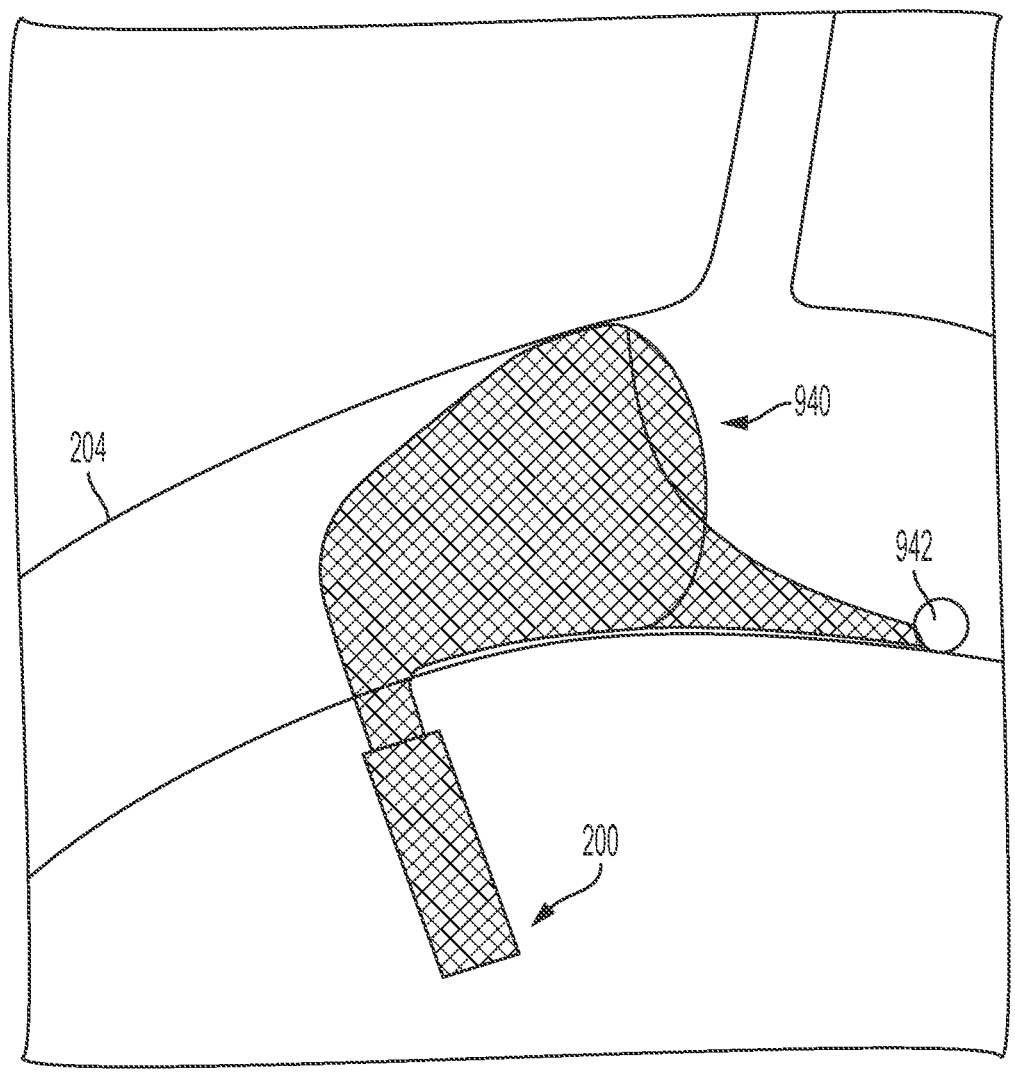
FIG. 25 is an illustration of a pump and expandable braided structure, according to some embodiments.

FIG. 25 is an illustration of a pump 200 and expandable braided structure 940, according to some embodiments. The pump 200 is configured to deploy within the access site and to force blood flow through the pump 200 and into the lumen of the main body. The pump 200 includes an expandable braided structure 940 configured to removably fix the pump 200 within the main body. The braided structure 940 may be configured to expand within the main body that is implanted within an aorta 204.

The braided structure 940 is configured to fixate the pump 200 within the main body or within the aorta 204 without the main body. The braided structure 940 may expand within a fenestration or portion of the main body. In certain instances, the braided structure 940 may expand to a diameter larger than the aorta 204, vessel, main body, or portal into which the braided structure 940 is implanted. The braided structure 940 may also act as an integrated filter. In certain instances, the braided structure 940 may include a membrane.

The braided structure 940 may include a snaring element 942 configured to facilitate collapsing of the braided structure 940 in response to tension. The snaring element 942 may be formed by terminating ends of the braided structure 940 forming a ring or other snareable structure. In other instances, the snaring element 942 may be a loop or ball coupled to the braided structure 940. Applying tension to the braided structure 940 collapses the braided structure 940 to enable removal and placement of the braided structure 940.

Figure 26:
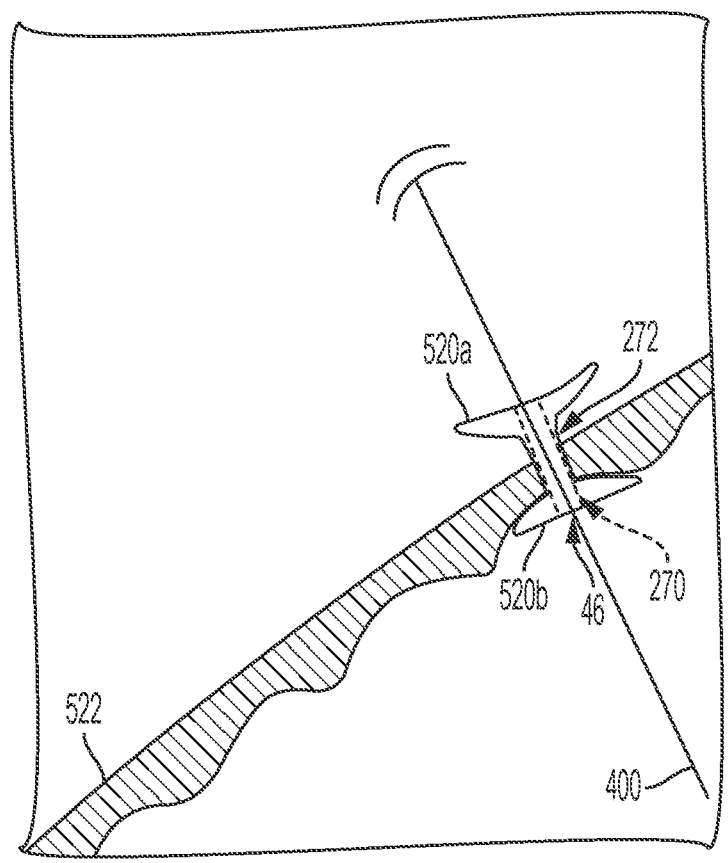
FIG. 26 is an illustration of an example shunt with flanges and a driveline arranged through the tissue anchor, according to some embodiments.

FIG. 26 is an illustration of an example shunt 270 with flanges 520a, 520 and a driveline 400 arranged through the shunt 270, according to some embodiments. Similar to the branch member 100 with flanges 520a, 520b discussed above with reference to FIG. 10, the shunt 270 is configured to engage a tissue wall 522. The tissue wall 522 may be the septum of a patient's hear tor along another portion of the heart wall. In certain instances, the shunt 270 is configured to provide a lumen 46 for a driveline 400.

The shunt 270, as shown in FIG. 26, may be positioned at a location along the tissue wall 522 of heart for the driveline 400 to cross and connect to a controller 500, as described in detail above, at one end, with the other end connected to a pump 200. In certain instances, the pump 200 may be located in another portion of the heart (e.g., left atrium connecting to the aorta) without an over docking mechanism such as the branch member 100 or other anchor system. In these instances, the shunt 270 may be used to anchor the driveline 400.

In certain instances, the lumen 46 is sized equal to or substantially equal to a circumference of the drive 400. In this manner, leakage does not occur through the lumen 46. The lumen 46 being sized equal to or substantially equal to a circumference of the driveline 400 allows for anchoring therein by, for example, a fiction or interference fit. The shunt 270 may be formed of a graft, a support structure (such as stent), or a combination thereof. In certain instances, the shunt 270 may be a coil of wire or film that may tighten about the driveline 400. In certain instances, the pump 200 may be directly or indirectly coupled to the shunt 270 as is explained in further detail below. In certain instances, the pump 200 being directly or indirectly coupled to the shunt 270 may establish a fluidic connection therebetween.

In certain instances, the flanges 520a, 520b may include a barrel portion 272 that connects that flanges 520a, 520b. The flanges 520a, 520b and the barrel portion 272 may be a uniform structure, in certain instances, and in other instances, the flanges 520a, 520b and the barrel portion 272 may be separate structures coupled to attached together prior to implantation. Similar to the branch member 100, the flanges 520a, 520b and the barrel portion 272 may include stent components, graft components, or a combination of stent and graft components.

Figure 27:
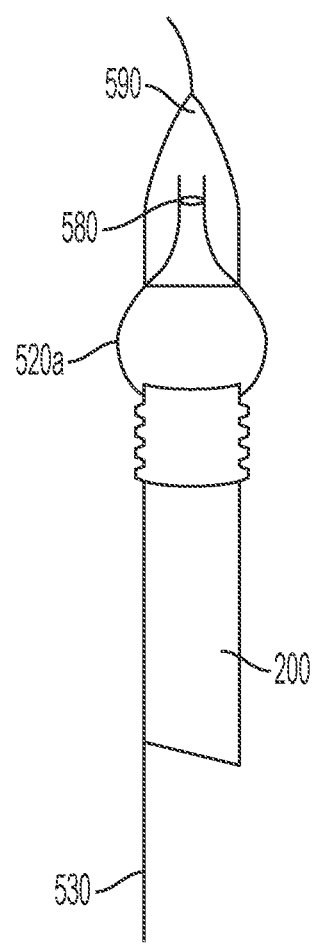
FIG. 27 is an illustration of another implantable medical device for cardiac assistance in a delivery configuration, according to some embodiments.

FIG. 27 is an illustration of another implantable medical device for cardiac assistance in a delivery configuration, according to some embodiments. As shown in FIG. 27, a pump 200 is arranged in a collapsed configuration for delivery. The pump 200 includes one or more flanges 520a, 520b (one flange is shown on an end of the pump 200 for ease of illustration), as is described in detail above. The flange 520a is collapsed toward the pump 200 in the delivery configuration. In certain instances, the flange 520a is held in the collapsed configuration by a lock wire 530 or similar mechanism. As shown, an end portion 580 of the lock wire 530 may be wrapped about the flange 520a. The flange 520a may be release by pulling back on the lock wire 530. In certain instances, the flange 520a may be held within a nose cone 590 rather than or in addition to the lock wire 530.

During delivery, the pump 200 and flange 520a is delivered, and when satisfactory positioning is achieved (e.g., within branch member 100), the lock wire 530 and/or the nose cone 590 is released.

In certain instances, the pump 200 and flange 520a may be arranged such that the flange 520a anchors the pump 200 within the atrial septum. The pump 200 may then be arranged across the pulmonary vein and configured to pull blood from the vein (and/or left atrium) thru the pump 200 for increased blood flow. The pump 200 may be arranged within a branch member 100 and within the pulmonary vein as is described in further detail above with reference to FIG. 14. An opposite end of the pump 200 (the side not anchored within the pulmonary vein) may extend into the aorta as also described in detail above.

Figure 28:
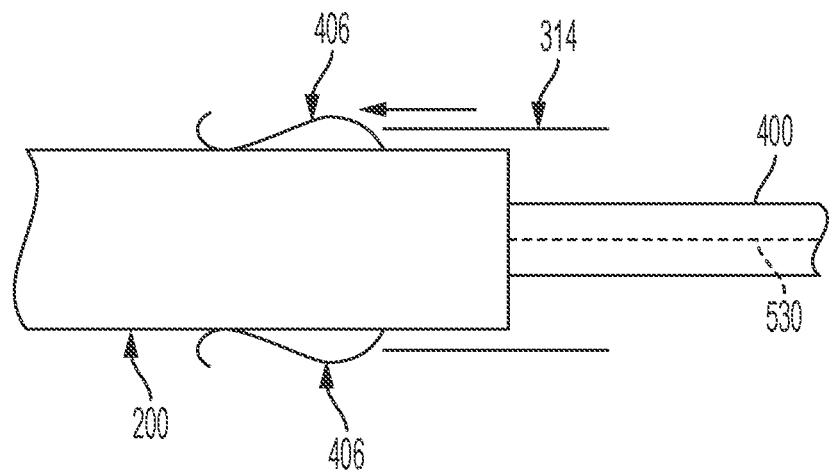
FIG. 28 is an illustration of a pump and delivery sheath, according to some embodiments.

FIG. 28 is an illustration of a pump 200 and delivery sheath 314, according to some embodiments. The pump 200 includes anchor elements 406 extending from an exterior surface of the pump 200. The anchor elements 406, as shown in FIG. 28, are s-hook elements that fit around or are integrated with the pump 200. The anchor elements 406 may be configured to either interference or friction fit the pump 200 within a branch member 100, or the branch member 100 may include a receiving structure as described in detail above (e.g., FIG. 22).

In certain instances, a delivery sheath 314 may depress or crush the anchor elements 406 against the pump 200 to allow for the pump 200 to deploy and/or be removed from the branch member 100.

In certain instances, a lock wire 530 may be arranged with and coupled to the pump 200. The lock wire 530 may be extend along the driveline 400. the lock wire 530 may form a portion of or can be integral with the driveline 400, or the lock wire 530 may be arranged within the driveline 400. The lock wire 530 may be pulled back to via the driveline 400 or separately from the driveline 400 to remove the pump 200. The pump 200 may be replaced or a new pump 200 may be reinstalled to continue functionality of the cardiac assistance device. Pulling on the lock wire 530 overcomes the anchor elements 406 and may remove the pump 200 from the branch member 100.

A biocompatible material for the graft components or membrane components, discussed herein, may be used. In certain instances, the graft may include a fluoropolymer, such as a polytetrafluoroethylene (PTFE) polymer or an expanded polytetrafluoroethylene (ePTFE) polymer. In some instances, the graft may be formed of a polyester, a silicone, a urethane, a polyethylene terephthalate, or another biocompatible polymer, or combinations thereof. In some instances, bioresorbable or bioabsorbable materials may be used, for example a bioresorbable or bioabsorbable polymer. In some instances, the graft can include Dacron, polyolefins, carboxy methylcellulose fabrics, polyurethanes, or other woven or film elastomers.

In addition, nitinol (NiTi) may be used as the material of the frame or stent (and any of the frames discussed herein), but other materials such as stainless steel, L605 steel, polymers, MP35N steel, polymeric materials, Pyhnox, Elgiloy, or any other appropriate biocompatible material, and combinations thereof, can be used as the material of the frame. The super-elastic properties and softness of NiTi may enhance the conformability of the stent. In addition, NiTi can be shape-set into a desired shape. That is, NiTi can be shape-set so that the frame tends to self-expand into a desired shape when the frame is unconstrained, such as when the frame is deployed out from a delivery system.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable medical device for cardiac assistance, the implantable medical device comprising:

a main body configured to be disposed within the aorta, the main body including a lumen operable to convey blood through the aorta;

an access site in a sidewall of the main body operable to provide access to the lumen of the main body; and a branch member configured to be disposed within the access site to fluidly connect with the lumen of the main body, the branch member includes one or more anchor elements configured to interface with and secure a pump with the branch member.

2. The implantable medical device of claim 1, wherein the branch member is configured to be disposed within an atrium or a ventricle of a patient.

3. The implantable medical device of claim 2, wherein the pump is configured to convey blood into the aorta from the atrium or ventricle for cardiac assistance through the branch member and into the main body.

4. The implantable medical device of claim 1, wherein the branch member includes a sealing element near a first end of the branch member, the sealing member configured to engage a tissue wall of a left atrium or a left ventricle.

5. The implantable medical device of claim 4, wherein the sealing element includes a flange configured to engage the tissue wall.

6. The implantable medical device of claim 1, wherein the access site in the main body includes a fenestration, wherein the branch member is configured to seal with the fenestration to fluidly connect the branch member and the main body.

7. The implantable medical device of claim 1, further comprising a portal arranged within a main lumen that is aligned with the access site in the main body, and a first portion of the branch member is configured to be disposed within the portal to fluidly connect the branch member and the main body.

8. The implantable medical device of claim 7, wherein a second portion of the branch member is configured to be disposed within the access site to fluidly connect with the lumen of the main body and a left atrial appendage of a heart.

9. The implantable medical device of claim 8, further including a stent structure coupled to the branch member or the pump and configured to stabilize the branch member or the pump within the left atrial appendage.

10. The implantable medical device of claim 9, wherein the branch member or the pump is arranged through an eyelet of the stent structure.

11. The implantable medical device of claim 10, wherein the stent structure defines an acorn shape or a shape that tapers toward a distal end.

12. The implantable medical device of claim 1, wherein the branch member is arranged about a patient's heart.

13. The implantable medical device of claim 1, wherein the pump includes one or more pump anchor elements, wherein the one or more branch anchor elements are operable for cooperative engagement with the one or more pump anchor elements and configured to anchor the pump with the branch member.

14. The implantable medical device of claim 1, wherein the one or more branch anchor elements are configured to frictionally engage the branch member and the pump to anchor the pump within the branch member.

15. A system for implanting an implantable medical device for cardiac assistance, the system com prising:

a first catheter configured to deploy an implantable medical device within an aorta, the implantable medical device including a main body, the main body including a lumen operable to maintain fluid flow through the aorta, the main body including an access site in a sidewall of the main body providing access to the lumen of the main body; and a second catheter configured to deploy a branch member within the access site to fluidly connect with the lumen of the main body and including a pump configured to convey blood through the branch member and into the lumen of the main body.

16. The system of claim 15, wherein the second catheter is configured to deploy the branch member transapically.

17. The system of claim 15, wherein the second catheter is configured to deploy the branch member transseptally.

18. The system of claim 15, further comprising a puncture device configured to create an access site in the aorta and an access site in an atrium or ventricle, and wherein the second catheter is configured to deploy the branch member across the access site in the aorta and the access site in an atrium or ventricle.

19. The system of claim 18, wherein the second catheter includes a sheath configured to deploy a flange arranged with a distal end of the branch member, the flange is configured to engage a tissue wall of the atrium or the ventricle in a fluid tight engagement.

20. An implantable medical device for cardiac assistance, the implantable medical device comprising:

a stent-graft having a main body having a lumen operable to convey blood therethrough and a branch member fluidly connected with the lumen of the main body, the branch member including one or more anchor elements;

an access site in a sidewall of the main body operable to provide access to the lumen of the main body;

a pump configured to deploy within a pulmonary vein and configured to interface with and secure with the one or more anchor elements of the branch member, the pump including a lumen configured to maintain blood flow through the pulmonary vein and configured to convey blood through the lumen.

21. The implantable medical device of claim 20, wherein the pump is configured to intake blood from the pulmonary vein and discharge the blood into the left atrium.

22. The implantable medical device of claim 20, wherein the pump is configured to increase flow out of the pulmonary vein to increase cardiac output.

23. The implantable medical device of claim 20, further comprising a driveline configured to power the pump, the driveline configured to extend out of the pulmonary vein into the left atrium and across a septum to exit a right side of the heart.

24. The implantable medical device of claim 20, wherein the driveline is operable to exit a patient via an iliac vein.

25. A method for cardiac assistance, the method com prising:

arranging an implantable medical device between an aorta and a heart chamber of a patient, the implantable medical device including a pump configured to convey blood from the heart chamber into the aorta; and forming a conduit of native tissue about the pump and between the aorta and the heart cham ber.

26. The method of claim 25, wherein forming the conduit of native tissue includes creating scarring or tissue ingrowth to farm a tissue layer between the aorta and the heart chamber.

27. The method of claim 25, wherein the pump includes a material arranged about an outer surface of the pump configured to facilitate tissue ingrowth.

28. The method of claim 27, wherein the material includes at least one of Dacron and ePTFE.

29. A medical device for cardiac assistance, the medical device comprising:
- a prosthetic valve comprising
  - a support frame,
  - a plurality of leaflets coupled to the support frame and configured to open to allow forward flow therethrough and to occlude the support frame to prevent retrograde flow, and
  - a pump arranged within the support frame and configured to convey blood through the support frame.

30. The medical device of claim 29, wherein the plurality of leaflets are configured to coapt about the pump.

31. The medical device of claim 30, wherein the pump is arranged centrally within the support frame.

32. The medical device of claim 29, further comprising a filter arranged at an outflow end of the support frame.

33. The medical device of claim 32, wherein the filter is arranged on an outflow end of the pump.

34. The medical device of claim 29, wherein the prosthetic valve is configured to replace an aortic valve of a patient.

35. The medical device of claim 29, wherein the prosthetic valve is configured to replace a mitral valve of a patient.

36. The medical device of claim 29, wherein the prosthetic valve and the pump are configured for transcatheter delivery.

37. An implantable medical device for cardiac assistance, the implantable medical device comprising:
- a main body configured to deploy within an aorta, the main body including a lumen configured to maintain fluid flow through the aorta;
- a branch member extending from the main body and configured to deploy within a chamber of a heart to fluidly connect the aorta and the chamber of the heart; and
- a pump arranged within the branch member and configured to convey blood from the chamber of the heart through the branch member and into the lumen of the main body.

38. The implantable medical device of claim 37, wherein the branch member is integral with the main body.

39. The implantable medical device of claim 38, wherein the branch member is configured to telescope inwardly and outwardly relative to the main body.

40. An implantable medical device for cardiac assistance, the implantable medical device comprising:
- a main body defining a lumen; and
- a stent-graft defining a branch member configured to deploy within a pulmonary vein and including a lumen configured to maintain fluid flow through the pulmonary vein and the lumen of the main body, the stent-graft configured to receive blood through the lumen; and
- a pump arranged within the branch member a pump arranged within the branch member to convey blood through the branch member, wherein the pump includes one or more anchor elements and is secured to the branch member via the one or more anchor elements.

41. The implantable medical device of claim 40, wherein the stent-graft is configured to interface with the pump, and the pump is configured to convey blood from the pulmonary vein to a left atrium.

42. The implantable medical device of claim 40, wherein the branch member includes one or more anchor elements, wherein the one or more pump anchor elements are operable for cooperative engagement with the one or more branch anchor elements and configured to anchor the pump with the branch member.

* * * * *